United States Patent
Tan

(10) Patent No.: US 9,463,426 B2
(45) Date of Patent: Oct. 11, 2016

(54) METHODS AND SYSTEMS FOR COATING PARTICLES

(75) Inventor: Sharon Mi Lyn Tan, Allston, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2338 days.

(21) Appl. No.: 11/165,949

(22) Filed: Jun. 24, 2005

(65) Prior Publication Data

US 2006/0292300 A1    Dec. 28, 2006

(51) Int. Cl.
| | |
|---|---|
| B01J 2/06 | (2006.01) |
| B01J 2/00 | (2006.01) |
| A61K 9/00 | (2006.01) |
| A61K 9/50 | (2006.01) |
| B01J 13/04 | (2006.01) |

(52) U.S. Cl.
CPC .............. *B01J 2/003* (2013.01); *A61K 9/0039* (2013.01); *A61K 9/5036* (2013.01); *A61K 9/5089* (2013.01); *B01J 2/06* (2013.01); *B01J 13/04* (2013.01)

(58) Field of Classification Search
USPC ........................................................ 427/212
See application file for complete search history.

(56) References Cited

U.S. PATENT DOCUMENTS

| | | |
|---|---|---|
| 2,275,154 A | 3/1942 | Merrill et al. |
| 2,609,347 A | 9/1952 | Wilson |
| 3,663,470 A | 5/1972 | Nishimura et al. |
| 3,737,398 A | 6/1973 | Yamaguchi |
| 3,930,076 A * | 12/1975 | Kliment ................. 427/353 |
| 3,957,933 A | 5/1976 | Egli et al. |
| 4,025,686 A | 5/1977 | Zion |
| 4,034,759 A | 7/1977 | Haerr |
| 4,055,377 A | 10/1977 | Erickson et al. |
| 4,076,640 A | 2/1978 | Forgensi et al. |
| 4,094,848 A | 6/1978 | Naito |
| 4,096,230 A | 6/1978 | Haerr |
| 4,098,728 A | 7/1978 | Rosenblatt |
| 4,110,529 A | 8/1978 | Stoy |
| 4,159,719 A | 7/1979 | Haerr |
| 4,191,672 A | 3/1980 | Salome et al. |
| 4,198,318 A | 4/1980 | Stowell et al. |
| 4,243,794 A | 1/1981 | White et al. |
| 4,246,208 A | 1/1981 | Dundas |
| 4,266,030 A | 5/1981 | Tschang et al. |
| 4,268,495 A | 5/1981 | Muxfeldt et al. |
| 4,271,281 A | 6/1981 | Kelley et al. |
| 4,402,319 A | 9/1983 | Handa et al. |
| 4,413,070 A | 11/1983 | Rembaum |
| 4,427,794 A | 1/1984 | Lange et al. |
| 4,428,869 A | 1/1984 | Munteanu et al. |
| 4,429,062 A | 1/1984 | Pasztor et al. |
| 4,442,843 A | 4/1984 | Rasor et al. |
| 4,444,961 A | 4/1984 | Timm |

(Continued)

FOREIGN PATENT DOCUMENTS

| | | |
|---|---|---|
| AU | A-76186/98 | 10/1998 |
| DE | 3834705 | 4/1990 |

(Continued)

OTHER PUBLICATIONS

U.S. Appl. No. 11/355,301, filed Feb. 15, 2006.

(Continued)

*Primary Examiner* — Robert Vetere

(57) ABSTRACT

Methods and systems for coating particles are disclosed.

3 Claims, 9 Drawing Sheets

(56) References Cited

U.S. PATENT DOCUMENTS

| | | | |
|---|---|---|---|
| 4,452,773 A | 6/1984 | Molday | |
| 4,456,693 A | 6/1984 | Welsh | |
| 4,459,145 A | 7/1984 | Elsholz | |
| 4,472,552 A | 9/1984 | Blouin | |
| 4,477,255 A | 10/1984 | Pasztor et al. | |
| 4,492,720 A | 1/1985 | Mosier | |
| 4,515,906 A | 5/1985 | Friesen et al. | |
| 4,522,953 A | 6/1985 | Barby et al. | |
| 4,542,178 A | 9/1985 | Zimmermann et al. | |
| 4,551,132 A | 11/1985 | Pasztor et al. | |
| 4,551,436 A | 11/1985 | Johnson et al. | |
| 4,568,559 A * | 2/1986 | Nuwayser et al. | 427/2.15 |
| 4,573,967 A | 3/1986 | Hargrove et al. | |
| 4,622,362 A | 11/1986 | Rembaum | |
| 4,623,706 A | 11/1986 | Timm et al. | |
| 4,629,464 A | 12/1986 | Takata et al. | |
| 4,640,807 A | 2/1987 | Afghan et al. | |
| 4,657,756 A | 4/1987 | Rasor et al. | |
| 4,661,137 A | 4/1987 | Garnier et al. | |
| 4,663,358 A | 5/1987 | Hyon et al. | |
| 4,671,954 A | 6/1987 | Goldberg et al. | |
| 4,674,480 A | 6/1987 | Lemelson | |
| 4,675,113 A | 6/1987 | Graves et al. | |
| 4,678,710 A | 7/1987 | Sakimoto et al. | |
| 4,678,814 A | 7/1987 | Rembaum | |
| 4,680,320 A | 7/1987 | Uku et al. | |
| 4,681,119 A | 7/1987 | Rasor et al. | |
| 4,695,466 A * | 9/1987 | Morishita et al. | 424/456 |
| 4,713,076 A | 12/1987 | Draenert | |
| 4,742,086 A | 5/1988 | Masamizu et al. | |
| 4,743,507 A | 5/1988 | Franses et al. | |
| 4,772,635 A | 9/1988 | Mitschker et al. | |
| 4,782,097 A | 11/1988 | Jain et al. | |
| 4,789,501 A | 12/1988 | Day et al. | |
| 4,793,980 A | 12/1988 | Torobin | |
| 4,795,741 A | 1/1989 | Leshchiner et al. | |
| 4,801,458 A | 1/1989 | Hidaka et al. | |
| 4,804,366 A | 2/1989 | Zdeb et al. | |
| 4,819,637 A | 4/1989 | Dormandy, Jr. et al. | |
| 4,822,535 A | 4/1989 | Ekman et al. | |
| 4,833,237 A | 5/1989 | Kawamura et al. | |
| 4,850,978 A | 7/1989 | Dudar et al. | |
| 4,859,711 A | 8/1989 | Jain et al. | |
| 4,863,972 A | 9/1989 | Itagaki et al. | |
| 4,897,255 A | 1/1990 | Fritzberg et al. | |
| 4,929,400 A | 5/1990 | Rembaum et al. | |
| 4,933,372 A | 6/1990 | Feibush et al. | |
| 4,946,899 A | 8/1990 | Kennedy et al. | |
| 4,954,399 A | 9/1990 | Tani et al. | |
| 4,981,625 A | 1/1991 | Rhim et al. | |
| 4,990,340 A | 2/1991 | Hidaka et al. | |
| 4,999,188 A | 3/1991 | Solodovnik et al. | |
| 5,007,940 A | 4/1991 | Berg | |
| 5,011,677 A | 4/1991 | Day et al. | |
| H915 H | 5/1991 | Gibbs | |
| 5,015,423 A | 5/1991 | Eguchi et al. | |
| 5,032,117 A | 7/1991 | Motta | |
| 5,034,324 A | 7/1991 | Shinozaki et al. | |
| 5,047,438 A | 9/1991 | Feibush et al. | |
| 5,079,274 A | 1/1992 | Schneider et al. | |
| 5,091,205 A | 2/1992 | Fan | |
| 5,106,903 A | 4/1992 | Vanderhoff et al. | |
| 5,114,421 A | 5/1992 | Polak | |
| 5,116,387 A | 5/1992 | Berg | |
| 5,120,349 A | 6/1992 | Stewart et al. | |
| 5,125,892 A | 6/1992 | Drudik | |
| 5,147,631 A | 9/1992 | Glajch et al. | |
| 5,147,937 A | 9/1992 | Frazza et al. | |
| 5,149,543 A | 9/1992 | Cohen et al. | |
| 5,158,573 A | 10/1992 | Berg | |
| 5,159,349 A * | 10/1992 | Endo et al. | 346/33 A |
| 5,171,214 A | 12/1992 | Kolber et al. | |
| 5,171,217 A | 12/1992 | March et al. | |
| 5,181,921 A | 1/1993 | Makita et al. | |
| 5,190,760 A | 3/1993 | Baker | |
| 5,190,766 A | 3/1993 | Ishihara | |
| 5,192,301 A | 3/1993 | Kamiya et al. | |
| 5,202,352 A | 4/1993 | Okada et al. | |
| 5,216,096 A | 6/1993 | Hattori et al. | |
| 5,253,991 A | 10/1993 | Yokota et al. | |
| 5,260,002 A | 11/1993 | Wang | |
| 5,262,176 A | 11/1993 | Palmacci et al. | |
| 5,263,992 A | 11/1993 | Guire | |
| 5,288,763 A | 2/1994 | Li et al. | |
| 5,292,814 A | 3/1994 | Bayer et al. | |
| 5,302,369 A | 4/1994 | Day et al. | |
| 5,314,974 A | 5/1994 | Ito et al. | |
| 5,316,774 A | 5/1994 | Eury et al. | |
| RE34,640 E | 6/1994 | Kennedy et al. | |
| 5,320,639 A | 6/1994 | Rudnick | |
| 5,328,936 A | 7/1994 | Leifholtz et al. | |
| 5,336,263 A | 8/1994 | Ersek et al. | |
| 5,344,452 A | 9/1994 | Lemperle | |
| 5,344,867 A | 9/1994 | Morgan et al. | |
| 5,354,290 A | 10/1994 | Gross | |
| 5,369,133 A | 11/1994 | Ihm et al. | |
| 5,369,163 A | 11/1994 | Chiou et al. | |
| 5,382,260 A | 1/1995 | Dormandy, Jr. et al. | |
| 5,384,124 A | 1/1995 | Courteille et al. | |
| 5,397,303 A | 3/1995 | Sancoff et al. | |
| 5,398,851 A | 3/1995 | Sancoff et al. | |
| 5,403,870 A | 4/1995 | Gross | |
| 5,417,982 A | 5/1995 | Modi | |
| 5,431,174 A | 7/1995 | Knute | |
| 5,435,645 A | 7/1995 | Faccioli et al. | |
| 5,443,495 A | 8/1995 | Buscemi et al. | |
| 5,456,693 A | 10/1995 | Conston et al. | |
| 5,468,801 A | 11/1995 | Antonelli et al. | |
| 5,469,854 A | 11/1995 | Unger et al. | |
| 5,476,472 A | 12/1995 | Dormandy, Jr. et al. | |
| 5,484,584 A | 1/1996 | Wallace et al. | |
| 5,490,984 A | 2/1996 | Freed | |
| 5,494,682 A | 2/1996 | Cohen et al. | |
| 5,494,940 A * | 2/1996 | Unger et al. | 521/66 |
| 5,512,604 A | 4/1996 | Demopolis | |
| 5,514,090 A | 5/1996 | Kriesel et al. | |
| 5,514,379 A | 5/1996 | Weissleder et al. | |
| 5,522,555 A * | 6/1996 | Poole | 241/33 |
| 5,525,334 A | 6/1996 | Ito et al. | |
| 5,534,589 A | 7/1996 | Hager et al. | |
| 5,541,031 A | 7/1996 | Yamashita et al. | |
| 5,542,935 A | 8/1996 | Unger et al. | |
| 5,553,741 A | 9/1996 | Sancoff et al. | |
| 5,556,391 A | 9/1996 | Cercone et al. | |
| 5,556,610 A | 9/1996 | Yan et al. | |
| 5,558,255 A | 9/1996 | Sancoff et al. | |
| 5,558,822 A | 9/1996 | Gitman et al. | |
| 5,558,856 A | 9/1996 | Klaveness et al. | |
| 5,559,266 A | 9/1996 | Klaveness et al. | |
| 5,567,415 A | 10/1996 | Porter | |
| 5,569,193 A | 10/1996 | Hofstetter et al. | |
| 5,569,449 A | 10/1996 | Klaveness et al. | |
| 5,569,468 A | 10/1996 | Modi | |
| 5,571,182 A | 11/1996 | Ersek et al. | |
| 5,580,575 A | 12/1996 | Unger et al. | |
| 5,583,162 A | 12/1996 | Li et al. | |
| 5,585,112 A | 12/1996 | Unger et al. | |
| 5,589,194 A * | 12/1996 | Tsuei et al. | 424/497 |
| 5,595,821 A | 1/1997 | Hager et al. | |
| 5,622,657 A | 4/1997 | Takada et al. | |
| 5,624,685 A | 4/1997 | Takahashi et al. | |
| 5,635,215 A | 6/1997 | Boschetti et al. | |
| 5,637,087 A | 6/1997 | O'Neil et al. | |
| 5,639,710 A | 6/1997 | Lo et al. | |
| 5,648,095 A | 7/1997 | Illum et al. | |
| 5,648,100 A | 7/1997 | Boschetti et al. | |
| 5,650,116 A | 7/1997 | Thompson | |
| 5,651,990 A | 7/1997 | Takada et al. | |
| 5,653,922 A | 8/1997 | Li et al. | |
| 5,657,756 A | 8/1997 | Vrba | |
| 5,681,576 A | 10/1997 | Henry | |
| 5,695,480 A | 12/1997 | Evans et al. | |
| 5,695,740 A | 12/1997 | Porter | |
| 5,698,271 A | 12/1997 | Liberti et al. | |

(56) References Cited

U.S. PATENT DOCUMENTS

| | | | |
|---|---|---|---|
| 5,701,899 A | 12/1997 | Porter | |
| 5,715,824 A | 2/1998 | Unger et al. | |
| 5,716,981 A | 2/1998 | Hunter et al. | |
| 5,718,884 A | 2/1998 | Klaveness et al. | |
| 5,723,269 A | 3/1998 | Akagi et al. | |
| 5,725,534 A | 3/1998 | Rasmussen | |
| 5,733,925 A | 3/1998 | Kunz et al. | |
| 5,741,331 A | 4/1998 | Pinchuk | |
| 5,746,734 A | 5/1998 | Dormandy, Jr. et al. | |
| 5,752,974 A | 5/1998 | Rhee et al. | |
| 5,756,127 A | 5/1998 | Grisoni et al. | |
| 5,760,097 A | 6/1998 | Li et al. | |
| 5,766,147 A | 6/1998 | Sancoff et al. | |
| 5,770,222 A | 6/1998 | Unger et al. | |
| 5,779,668 A | 7/1998 | Grabenkort | |
| 5,785,642 A | 7/1998 | Wallace et al. | |
| 5,785,682 A | 7/1998 | Grabenkort | |
| 5,792,478 A | 8/1998 | Lawin et al. | |
| 5,795,562 A | 8/1998 | Klaveness et al. | |
| 5,797,953 A | 8/1998 | Tekulve | |
| 5,807,323 A | 9/1998 | Kriesel et al. | |
| 5,813,411 A | 9/1998 | Van Bladel et al. | |
| 5,823,198 A | 10/1998 | Jones et al. | |
| 5,827,502 A | 10/1998 | Klaveness et al. | |
| 5,827,531 A | 10/1998 | Morrison et al. | |
| 5,830,178 A | 11/1998 | Jones et al. | |
| 5,833,361 A | 11/1998 | Funk | |
| 5,840,387 A | 11/1998 | Berlowitz-Tarrant et al. | |
| 5,846,518 A | 12/1998 | Yan et al. | |
| 5,853,752 A | 12/1998 | Unger et al. | |
| 5,855,615 A | 1/1999 | Bley et al. | |
| 5,863,957 A | 1/1999 | Li et al. | |
| 5,876,372 A | 3/1999 | Grabenkort et al. | |
| 5,877,224 A | 3/1999 | Brocchini et al. | |
| 5,885,216 A | 3/1999 | Evans, III et al. | |
| 5,885,547 A | 3/1999 | Gray | |
| 5,888,538 A | 3/1999 | Kiefer et al. | |
| 5,888,546 A | 3/1999 | Ji et al. | |
| 5,888,930 A | 3/1999 | Smith et al. | |
| 5,891,155 A | 4/1999 | Irie | |
| 5,894,022 A | 4/1999 | Ji et al. | |
| 5,895,398 A | 4/1999 | Wensel et al. | |
| 5,895,411 A | 4/1999 | Irie | |
| 5,899,877 A | 5/1999 | Leibitzki et al. | |
| 5,902,832 A | 5/1999 | Van Bladel et al. | |
| 5,902,834 A | 5/1999 | Porrvik | |
| 5,922,025 A | 7/1999 | Hubbard | |
| 5,922,304 A | 7/1999 | Unger | |
| 5,928,626 A | 7/1999 | Klaveness et al. | |
| 5,935,553 A | 8/1999 | Unger et al. | |
| 5,951,160 A | 9/1999 | Ronk | |
| 5,957,848 A | 9/1999 | Sutton et al. | |
| 5,959,073 A | 9/1999 | Schlameus et al. | |
| 6,003,566 A | 12/1999 | Thibault et al. | |
| 6,015,546 A | 1/2000 | Sutton et al. | |
| 6,015,773 A * | 1/2000 | Wysong et al. | 504/360 |
| 6,027,472 A | 2/2000 | Kriesel et al. | |
| 6,028,066 A | 2/2000 | Unger | |
| 6,047,861 A | 4/2000 | Vidal et al. | |
| 6,048,908 A | 4/2000 | Kitagawa | |
| 6,051,247 A | 4/2000 | Hench et al. | |
| 6,056,721 A | 5/2000 | Shulze | |
| 6,056,844 A | 5/2000 | Guiles et al. | |
| 6,059,766 A | 5/2000 | Greff | |
| 6,063,068 A | 5/2000 | Fowles et al. | |
| 6,071,495 A | 6/2000 | Unger et al. | |
| 6,071,497 A | 6/2000 | Steiner et al. | |
| 6,073,759 A | 6/2000 | Lamborne et al. | |
| 6,090,925 A | 7/2000 | Woiszwillo et al. | |
| 6,096,344 A | 8/2000 | Liu et al. | |
| 6,099,864 A | 8/2000 | Morrison et al. | |
| 6,100,306 A | 8/2000 | Li et al. | |
| 6,139,963 A | 10/2000 | Fujii et al. | |
| 6,149,623 A | 11/2000 | Reynolds | |
| 6,160,084 A | 12/2000 | Langer et al. | |
| 6,162,377 A | 12/2000 | Ghosh et al. | |
| 6,165,193 A | 12/2000 | Greene, Jr. et al. | |
| 6,179,817 B1 | 1/2001 | Zhong | |
| 6,191,193 B1 | 2/2001 | Lee et al. | |
| 6,214,331 B1 | 4/2001 | Vanderhoff et al. | |
| 6,214,384 B1 | 4/2001 | Pallado et al. | |
| 6,224,630 B1 | 5/2001 | Bao et al. | |
| 6,224,794 B1 | 5/2001 | Amsden et al. | |
| 6,235,224 B1 | 5/2001 | Mathiowitz et al. | |
| 6,238,403 B1 | 5/2001 | Greene, Jr. et al. | |
| 6,245,090 B1 | 6/2001 | Gilson et al. | |
| 6,251,661 B1 | 6/2001 | Urabe et al. | |
| 6,258,338 B1 | 7/2001 | Gray | |
| 6,261,585 B1 | 7/2001 | Sefton et al. | |
| 6,264,861 B1 | 7/2001 | Tavernier et al. | |
| 6,267,154 B1 | 7/2001 | Felicelli et al. | |
| 6,268,053 B1 | 7/2001 | Woiszwillo et al. | |
| 6,277,392 B1 | 8/2001 | Klein | |
| 6,280,457 B1 | 8/2001 | Wallace et al. | |
| 6,291,605 B1 | 9/2001 | Freeman et al. | |
| 6,296,604 B1 | 10/2001 | Garibaldi et al. | |
| 6,296,622 B1 | 10/2001 | Kurz et al. | |
| 6,296,632 B1 | 10/2001 | Luscher et al. | |
| 6,306,418 B1 | 10/2001 | Bley | |
| 6,306,419 B1 | 10/2001 | Vachon et al. | |
| 6,306,425 B1 | 10/2001 | Tice et al. | |
| 6,306,427 B1 | 10/2001 | Annonier et al. | |
| 6,312,407 B1 | 11/2001 | Zadno-Azizi et al. | |
| 6,312,942 B1 | 11/2001 | Plüss-Wenzinger et al. | |
| 6,315,709 B1 | 11/2001 | Garibaldi et al. | |
| 6,335,384 B1 | 1/2002 | Evans et al. | |
| 6,344,182 B1 | 2/2002 | Sutton et al. | |
| 6,355,275 B1 | 3/2002 | Klein | |
| 6,368,658 B1 | 4/2002 | Schwarz et al. | |
| 6,379,373 B1 | 4/2002 | Sawhney et al. | |
| 6,388,043 B1 | 5/2002 | Langer et al. | |
| 6,394,965 B1 | 5/2002 | Klein | |
| 6,423,332 B1 | 7/2002 | Huxel et al. | |
| 6,432,437 B1 | 8/2002 | Hubbard | |
| 6,436,112 B2 | 8/2002 | Wensel et al. | |
| 6,443,941 B1 | 9/2002 | Slepian et al. | |
| 6,458,296 B1 * | 10/2002 | Heinzen et al. | 264/9 |
| 6,476,069 B2 | 11/2002 | Krall et al. | |
| 6,495,155 B1 | 12/2002 | Tice et al. | |
| 6,544,503 B1 | 4/2003 | Vanderhoff et al. | |
| 6,544,544 B2 | 4/2003 | Hunter et al. | |
| 6,545,097 B2 | 4/2003 | Pinchuk et al. | |
| 6,575,896 B2 | 6/2003 | Silverman et al. | |
| 6,602,261 B2 | 8/2003 | Greene, Jr. et al. | |
| 6,602,524 B2 | 8/2003 | Batich et al. | |
| 6,605,111 B2 | 8/2003 | Bose et al. | |
| 6,629,947 B1 | 10/2003 | Sahatjian et al. | |
| 6,632,531 B2 | 10/2003 | Blankenship | |
| 6,652,883 B2 | 11/2003 | Goupil et al. | |
| 6,680,046 B1 | 1/2004 | Boschetti | |
| 6,699,222 B1 | 3/2004 | Jones et al. | |
| 7,591,993 B2 | 9/2009 | Boschetti | |
| 2001/0001835 A1 | 5/2001 | Greene, Jr. et al. | |
| 2001/0016210 A1 | 8/2001 | Mathiowitz et al. | |
| 2001/0036451 A1 | 11/2001 | Goupil et al. | |
| 2001/0051670 A1 | 12/2001 | Goupil et al. | |
| 2002/0054912 A1 * | 5/2002 | Kim et al. | 424/489 |
| 2002/0061954 A1 | 5/2002 | Davis et al. | |
| 2002/0160109 A1 | 10/2002 | Yeo et al. | |
| 2002/0182190 A1 | 12/2002 | Naimark et al. | |
| 2002/0197208 A1 | 12/2002 | Ruys et al. | |
| 2003/0007928 A1 | 1/2003 | Gray | |
| 2003/0032935 A1 | 2/2003 | Damiano et al. | |
| 2003/0047676 A1 * | 3/2003 | Grier et al. | 250/251 |
| 2003/0108614 A1 | 6/2003 | Volkonsky et al. | |
| 2003/0183962 A1 | 10/2003 | Buiser et al. | |
| 2003/0185895 A1 * | 10/2003 | Lanphere et al. | 424/493 |
| 2003/0185896 A1 | 10/2003 | Buiser et al. | |
| 2003/0187320 A1 | 10/2003 | Freyman | |
| 2003/0194390 A1 | 10/2003 | Krall et al. | |
| 2003/0203985 A1 | 10/2003 | Baldwin et al. | |
| 2003/0206864 A1 | 11/2003 | Mangin | |
| 2003/0215519 A1 | 11/2003 | Schwarz et al. | |
| 2003/0233150 A1 | 12/2003 | Bourne et al. | |

(56) References Cited

U.S. PATENT DOCUMENTS

| | | | |
|---|---|---|---|
| 2004/0009219 A1* | 1/2004 | Odidi et al. ............... | 424/468 |
| 2004/0076582 A1 | 4/2004 | DiMatteo et al. | |
| 2004/0091543 A1 | 5/2004 | Bell et al. | |
| 2004/0092883 A1 | 5/2004 | Casey, III et al. | |
| 2004/0096662 A1 | 5/2004 | Lanphere et al. | |
| 2004/0101564 A1 | 5/2004 | Rioux et al. | |
| 2004/0131669 A1* | 7/2004 | Kerc ............................ | 424/454 |
| 2004/0186377 A1 | 9/2004 | Zhong et al. | |
| 2005/0025800 A1 | 2/2005 | Tan | |
| 2005/0037047 A1 | 2/2005 | Song | |
| 2005/0095428 A1 | 5/2005 | DiCarlo et al. | |
| 2005/0129775 A1 | 6/2005 | Lanphere et al. | |
| 2005/0196449 A1 | 9/2005 | DiCarlo et al. | |
| 2005/0226935 A1 | 10/2005 | Kamath et al. | |
| 2005/0238870 A1 | 10/2005 | Buiser et al. | |
| 2005/0263916 A1 | 12/2005 | Lanphere et al. | |
| 2006/0045900 A1 | 3/2006 | Richard et al. | |
| 2006/0116711 A1 | 6/2006 | Elliott et al. | |
| 2006/0173090 A1 | 8/2006 | Baldwin et al. | |
| 2006/0199009 A1 | 9/2006 | Anderson et al. | |
| 2006/0199010 A1 | 9/2006 | DiCarlo et al. | |
| 2006/0210710 A1 | 9/2006 | Buiser et al. | |
| 2006/0247610 A1 | 11/2006 | Lanphere et al. | |
| 2007/0004973 A1 | 1/2007 | Tan | |
| 2007/0059375 A1 | 3/2007 | Bourne et al. | |
| 2007/0083219 A1 | 4/2007 | Buiser et al. | |
| 2007/0083226 A1 | 4/2007 | Buiser et al. | |
| 2007/0142859 A1 | 6/2007 | Buiser et al. | |
| 2007/0142893 A1 | 6/2007 | Buiser et al. | |

FOREIGN PATENT DOCUMENTS

| | | |
|---|---|---|
| DE | 94 14 868.6 | 12/1994 |
| DE | 297 24 255 U1 | 10/2000 |
| DE | 100 26 620 | 3/2002 |
| EP | 0 067 459 | 12/1982 |
| EP | 0 122 624 | 10/1984 |
| EP | 0 123 235 | 10/1984 |
| EP | 0 243 165 | 10/1987 |
| EP | 0 294 206 | 12/1988 |
| EP | 0 402 031 | 12/1990 |
| EP | 0 422 258 | 4/1991 |
| EP | 0 458 079 | 11/1991 |
| EP | 0 458 745 | 11/1991 |
| EP | 0 470 569 | 2/1992 |
| EP | 0 547 530 | 6/1993 |
| EP | 0 600 529 | 6/1994 |
| EP | 0 623 012 | 11/1994 |
| EP | 0 706 376 | 4/1996 |
| EP | 0 730 847 | 9/1996 |
| EP | 0 744 940 | 12/1996 |
| EP | 0 764 047 | 3/1997 |
| EP | 0 797 988 | 10/1997 |
| EP | 0 993 337 | 4/2000 |
| ES | 2 096 521 | 3/1997 |
| JP | 59-196738 | 11/1984 |
| JP | 62-45637 | 2/1987 |
| JP | 4-74117 | 3/1992 |
| JP | 6-57012 | 3/1994 |
| JP | 9-110678 | 4/1997 |
| JP | 9-165328 | 6/1997 |
| JP | 9-316271 | 12/1997 |
| JP | 10-130329 | 5/1998 |
| JP | 2000189511 | 7/2000 |
| JP | 2001079011 | 3/2001 |
| JP | 2002-017848 | 1/2002 |
| NZ | 255409 | 2/1997 |
| NZ | 517377 | 8/2003 |
| TW | 421658 | 2/2001 |
| WO | WO 91/12823 | 5/1991 |
| WO | WO 92/21327 | 12/1992 |
| WO | WO 93/00063 | 1/1993 |
| WO | WO 93/19702 | 10/1993 |
| WO | WO 94/10936 | 5/1994 |
| WO | WO 95/03036 | 2/1995 |
| WO | WO 95/22318 | 8/1995 |
| WO | WO 95/33553 | 12/1995 |
| WO | WO 96/37165 | 11/1996 |
| WO | WO 96/39464 | 12/1996 |
| WO | WO 98/04616 | 2/1998 |
| WO | WO 98/10798 | 3/1998 |
| WO | WO 98/26737 | 6/1998 |
| WO | WO 98/47532 | 10/1998 |
| WO | WO 99/00187 | 1/1999 |
| WO | WO 99/12577 | 3/1999 |
| WO | WO 99/43380 | 9/1999 |
| WO | WO 99/51278 | 10/1999 |
| WO | WO 99/57176 | 11/1999 |
| WO | WO 00/23054 | 4/2000 |
| WO | WO 00/32112 | 6/2000 |
| WO | WO 00/40259 | 7/2000 |
| WO | 00/66183 | 11/2000 |
| WO | WO 00/71196 | 11/2000 |
| WO | WO 00/74633 | 12/2000 |
| WO | WO 01/12359 | 2/2001 |
| WO | WO 01/66016 | 9/2001 |
| WO | WO 01/70291 | 9/2001 |
| WO | WO 01/72281 | 10/2001 |
| WO | WO 01/76845 | 10/2001 |
| WO | WO 01/93920 | 12/2001 |
| WO | WO 02/11696 | 2/2002 |
| WO | WO 02/34298 | 5/2002 |
| WO | WO 02/34299 | 5/2002 |
| WO | WO 02/34300 | 5/2002 |
| WO | WO 02/43580 | 6/2002 |
| WO | WO 03/013552 | 2/2003 |
| WO | WO 03/016364 | 2/2003 |
| WO | WO 03/051451 | 6/2003 |
| WO | WO 03/082359 | 10/2003 |
| WO | WO 2004/014446 | 2/2004 |
| WO | WO 2004/019999 | 3/2004 |
| WO | WO 2004/040972 | 5/2004 |
| WO | WO 2004/073688 | 9/2004 |
| WO | WO 2004/075989 | 9/2004 |
| WO | WO 2005/118128 | 12/2005 |

OTHER PUBLICATIONS

U.S. Appl. No. 11/425,546, filed Jun. 21, 2006.
U.S. Appl. No. 11/428,907, filed Jul. 6, 2006.
U.S. Appl. No. 11/430,602, filed May 9, 2006.
U.S. Appl. No. 11/458,156, filed Jul. 18, 2006.
U.S. Appl. No. 11/458,171, filed Jul. 18, 2006.
U.S. Appl. No. 60/820,503, filed Jul. 27, 2006.
U.S. Appl. No. 60/820,504, filed Jul. 27, 2006.
U.S. Appl. No. 60/822,545, filed Aug. 16, 2006.
U.S. Appl. No. 60/856,662, filed Nov. 3, 2006.
U.S. Appl. No. 60/866,242, filed Nov. 17, 2006.
U.S. Appl. No. 60/870,238, filed Dec. 15, 2006.
U.S. Appl. No. 60/905,023, filed Mar. 5, 2007.
U.S. Appl. No. 11/248,033, filed Oct. 12, 2005.
U.S. Appl. No. 11/248,493, filed Oct. 12, 2005.
U.S. Appl. No. 11/311,617, filed Dec. 19, 2005.
U.S. Appl. No. 11/314,056, filed Dec. 21, 2005.
U.S. Appl. No. 11/314,557, filed Dec. 21, 2005.
U.S. Appl. No. 10/927,868, filed Aug. 27, 2004, Richard et al.
U.S. Appl. No. 11/000,741, filed Dec. 1, 2004, Elliott et al.
U.S. Appl. No. 11/070,967, filed Mar. 2, 2005, Anderson et al.
U.S. Appl. No. 11/111,511, filed Apr. 21, 2005, DiCarlo et al.
U.S. Appl. No. 11/117,156, filed Apr. 28, 2005, Lanphere et al.
U.S. Appl. No. 11/154,106, filed Jun. 15, 2005, Tan.
Abbara et al., "Transcervical Expulsion of a Fibroid as a Result of Uterine Artery Embolization for Leiomyomata", *JVIR*, vol. 10, No. 4, pp. 409-411, 1999.
Abrahams, J.M. et al., "Topic Review: Surface Modifications Enhancing Biological Activity of Guglielmi Detachable Coils in Treating Intracranial Aneurysms", *Surg. Neurol.* 54:34-41, 2000.
Abrahams, J.M. et al., "Delivery of Human Vascular Endothelial Growth Factor with Platinum Coils Enhances Wall Thickening and Coil Impregnation in a Rat Aneurysm Model", *AJNR Am. J. Neuroradiol.* 22:1410-1417, Aug. 2001.

(56) References Cited

OTHER PUBLICATIONS

Ahuja, A.A., "Platinum Coil Coatings to Increase Thrombogenicity: A Preliminary Study in Rabbits", *AJNR Am. J. Neuroradiol.* 14:794-798; Jul./Aug. 1993.
Antibody Labeling, http://www.altcorp.com/AffinityLabeling/ablaeling.htm, pp. 1-6, May 20, 2003.
Bachtsi, A.R. et al., "An Experimental Investigation of Enzyme Release from Poly(vinyl alcohol) crosslinked Microspheres", *J. Microencapsulation*, vol. 12, No. 1, pp. 23-35; 1995.
Barr, J.D., et al., "Polyvinyl Alcohol Foam Particles Sizes and Concentrations Injectable through Microcatheters", *JVIR*, vol. 9, No. 1, pp. 113-118; 1998.
Barton, P. et al., "Embolization of Bone Metastases," *Journal of Vascular and Interventional Radiology*, 7(1):81-88 (Jan.-Feb. 1996).
Battinelli, L. et al., "New Class of Poly(vinyl alcohol) Polymrs as Column-Chromatography Stationary Phases for Candida Rugosa Lipase Isoforms Separation", *J. Chromatogr A*, vol. 753, No. 1, pp. 47-55; 1996.
Beaujeux, R. et al., "Trisacryl Gelatin Microspheres for Therapeutic Embolization, II: Preliminary Clinical Evaluation in Tumors and Arteriovenous Malformations," *AJNR Am. J. Neuroradiol.*, 17:541-548, Mar. 1996.
Berenstein, A. et al., "Catheter and Material Selection for Transarterial Embolization: Technical Considerations. II. Materials.", *Radiology*, vol. 132, No. 3, pp. 631-639; 1979.
Berenstein, A. et al., "Microembolization Techniques of Vascular Occlusion: Radiologic, Patohologic, and Clinical Correlation", *AJNR Am I Neuroradiol*, vol. 2, No. 3, pp. 261-267; 1981.
Berkowitz, R.P. et al., "Vaginal Expulsion of Submucosal Fibroids After Uterine Artery Embolization", *Journal of Reproductive Medicine*, vol. 44, No. 4, pp. 373-376; Apr. 1999 http://www.reproductivemedicine.com.
Bourke et al., "Protein Drug Release from Photocrosslinked Poly-(vinyl alcohol) Hydrogels," *Society for Biomaterials 28th Annual Meeting Transactions*, p. 144 (2002).
Bradley, E.A. et al., "Transcatheter Uterine Artery Embolisation to Treat Large Uterine Fibroids", *British Journal of Obstetrics and Gynaecology*, vol. 105, pp. 235-240; Feb. 1998.
Brockmann, J. et al., "Radiolabeling of p-Bz-DOTA-CD-11c antibody with $^{88}$Y: Conjugation, Labeling, Biodistribution studies", 2 pages, 2000 http://www.kernchemie.uni-mainz.de/downloads/jb2000/b14_brockmann.pdf.
Bruix, J. et al., "Transarterial Embolization Versus Symptomatic Treatment in Patients With Advanced Hepatocellular Carcinoma: Results of a Randomized, Controlled Trial in a Single Institution", *Hepatology*, Jun. 1998, vol. 27, No. 6, pp. 1578-1583, http://www.hepatitis-central.com/hcv/hcc/embolization/references.html.
Buhle, Jr. EL, "Re: Re: Hepatic Arterial Embolization", *UCLA Medicine Online*, Mar. 10, 1996, http://www.meds.com/archive/mol-cancer/1996/msg00128.html, 2 pages.
Burczak, et al., "Long-term in vivo performance and biocompatibility of poly (vinyl alcohol) hydrogel macrocapsules for hybrid-type artificial pancreas", *Biomaterials*, vol. 17, No. 24, pp. 2351-2356, 1996.
Burczak, et al., "Polymeric materials for biomedical purposes obtained by radiation methods. V. hybrid artificial pancreas", *Polim Med*, vol. 24, No. 1-2, pp. 45-55, 1994 (English Summary included).
Capozza et al., "Endoscopic treatment of vesico-ureteric reflux and urinary incontinence: technical problems in the paediatric patient," *British Journal of Urology*, 75(4):538-542 (Apr. 1995).
Carroll, B.A. et al., "Microbubbles as Ultrasonic Contrast Agents", *Investigative Radiology*, vol. 14, No. 3, p. 374, Supplement to May-Jun. 1979.
Carroll, B.A. et al., "Gelatin Encapsulated Nitrogen Microbubbles as Ultrasonic Contrast Agents", *Journal of Clinical and Laboratory Research*, vol. 15, No. 1, pp. 260-266, Feb. 1980.
Carstensen, E.L. et al., "Determination of the Acoustic Properties of Blood and its Components", *Journal of Acoustical Society of America*, vol. 25, No. 2, pp. 286-289, Mar. 1953.
Choe, et al., "An experimental study of embolic effect according to infusion rate and concentration of suspension in transarterial particulate embolization", *Invest Radiol*, vol. 32, No. 5, pp. 260-270, 1997.
Chuang et al., "Experimental Canine Hepatic Artery Embolization with Polyvinyl Alcohol Foam Particles", *Departments of Diagnostic Radiology and Veterinary Medicine*, The University of Texas, M.D. Anderson Hospital and Tumor Institute at Houston, Texas, pp. 21-25, Oct. 1982.
Cirkel, U. et al., "Experience with Leuprorelin Acetate Depot in the Treatment of Fibroids: A German Multicentre Study", *Clinical Therapeutics*, vol. 14, Suppl. A, 1992.
Clarian Health Methodist—Indiana Lions Gamma Knife Center, "Arteriovenous Malformation," http://www.clarian.com/tyhealth/gammaknife/cond_arter.asp, 4 pages, Last Updated on Mar. 20, 2000.
Colombo M, "Treatment of Hepatocellular Carcinoma", *Journal of Viral Hepatitis*, 4(Suppl. 1):125-130 (1997), http://home.texoma.net/~moreland/stats/hcc-9.html.
Concentric Medical, Inc.—Product Information (3 pages), 2002.
Cruise et al., "In Vitro and In Vivo Characterization of a Hydrogel-Based Aneurysm Embolization System," *Society for Biomaterials 28th Annual Meeting Transactions*, p. 203 (2002).
Deasy, P. B., "*Microencapsulation and Related Drug Processes*", New York, NY, Marcel Dekker, Inc., 345 pages, 1984 (Table of Contents only).
de Gast, A.N. et al., "Transforming Growth Factor β-coated Platinum Coils for Endovascular Treatment of Aneurysms: An Animal Study", *Neurosurgery*, vol. 49, No. 3, pp. 690-696, Sep. 2001.
Derdeyn, et al., "Collagen-coated acrylic microspheres for embolotherapy: in vivo and in vitro characteristics", *American Journal of Neuroradiology*, vol. 18, No. 4, pp. 647-653, 1997.
Derdeyn, et al., "Polyvinyl alcohol particle size and suspension characteristics", *American Journal of Neuroradiology*, vol. 16, pp. 1335-1343, 1995.
DiLuccio et al., "Sustained-Release Oral Delivery of Theophylline by Use of Polyvinyl Alcohol and Polyvinyl Alcohol-Methyl Acrylate Polymers", *Journal of Pharmaceutical Sciences*, vol. 83, No. 1, pp. 104-106, Jan. 1994.
Duckwiler et al., "Catheters, embolic agents spark neurointervention," *Diagnostic Imaging*, 16(5):66-72 (May 1994).
Ersek et al., "Bioplastique: A New Textured Copolymer Microparticle Promises Permanence in Soft-Tissue Augmentation," *Plastic and Reconstructive Surgery*, 87(4):693-702 (Apr. 1991).
Eskridge, "Interventional Neuroradiology," *Radiology*, 172:991-1006 (Nov. 1989).
Feldman, L. et al., "Transcatheter Vessel Occlusion: Angiographic Results Versus Clinical Success", *Radiology*, vol. 147, pp. 1-5, Apr. 1983.
Ferrofluids, Physical Properties and Applications Ferrofluidics Corp., Nashua, NH, 5 pages, 1986.
FeRx Incorporated, FERX Profile http://www.biotechshares.com/FERX.htm, 4 pages (Retrieved from the internet on Jun. 26, 2003).
"Fibroid Treatment Collective—Fibroid Embolization," 2 pages, http://www.fibroids.org.
Fritzsch, T. et al., "SH U 508, A Transpulmonary Echocontrast Agent", *Investigative Radiology*, vol. 25, Supplement 1, pp. S160-S161, Sep. 1990.
Fujimoto, S. et al., "Biodegradable Mitomycin C Microspheres Given Intra-Arterially for Inoperable Hepatic Cancer", *Cancer*, vol. 56, pp. 2404-2410, 1985.
Gander, et al., "Effect of polymeric network structure on drug release from cross-linked poly(vinyl alcohol) micromatrices", *Pharm Res*, vol. 6, No. 7, pp. 578-584, 1989.
Germano, et al., "Histopathological follow-up study of 66 cerebral arteriovenous malformations after therapeutic embolization with polyvinyl alcohol", *J Neurosurg*, vol. 76, No. 4, pp. 607-614, 1992.
Geschwind et al., "Chemoembolization of Liver Tumor in a Rabbit Model: Assessment of Tumor Cell Death with Diffusion-Weighted MR Imaging and Histologic Analysis", *Journal of Vascular and Interventional Radiology*, vol. 11, No. 10, pp. 1244-1255, Dec. 2000.

(56) References Cited

OTHER PUBLICATIONS

Gilbert, W.M. et al., "Angiographic Embolization in the Management of Hemorrhagic Complications of Pregnancy", *American Journal of Obstetrics and Gynecology*, vol. 166, No. 2, pp. 493-497, Feb. 1992.

Gohel, et al., "Formulation design and optimization of modified-release microspheres of diclofenac sodium", *Drug Dev Ind Pharm*, vol. 25, No. 2, pp. 247-251, 1999.

Goldberg, B.B., "Ultrasonic Cholangiography", *Radiology*, vol. 118, pp. 401-404, Feb. 1976.

Goodwin, et al., "Overview of embolic agents and their indications", *Eleventh Annual International Symposium on Endovascular Therapy*, pp. 303-306, 1999.

Goodwin, et al., "Preliminary experience with uterine artery embolization for uterine fibroids", *Journal of Vascular and Interventional Radiology*, vol. 8, No. 4, pp. 517-526, 1997.

Gramiak et al., "Echocardiography of the Aortic Root," *Investigative Radiology*, 3(5):356-366 (Sep.-Oct. 1968).

Gramiak, R. et al., "Ultrasound Cardiography: Contrast Studies in Anatomy and Function", *Radiology*, vol. 92, No. 5, pp. 939-948, Apr. 1969.

Grandfils, et al., "Preparation of poly (D,L) lactide microspheres by emulsion solvent evaporation, and their clinical implications as a convenient embolic material", *J Biomed Mater Res*, vol. 26, No. 4, pp. 467-479, 1992.

Greenwood, L.H. et al., "Obstetric and Nonmalignant Gynecologic Bleeding: Treatment with Angiographic Embolization", *Radiology*, vol. 164, No. 1, pp. 155-159, Jul. 1987.

Gupta et al., "Plasma-induced graft polymerization of acrylic acid onto poly(ethylene terephthalate) films: characterization and human smooth muscle cell growth on grafted films," *Biomaterials*, 23:863-871 (2002).

Halstenberg et al., "Biologically Engineered Protein-*graft*-Poly(ethylene glycol) Hydrogels: A Cell Adhesive and Plasmin-Degradable Biosynthetic Material for Tissue Repair," *Biomacromolecules*, 3(4):710-723 (2002).

Hamada et al., "Embolization with Cellulose Porous Beads, II: Clinical Trial," *AJNR Am. J. Neuroradiol.*, 17:1901-1906 (Nov. 1996).

Hirano et al., "Transcutaneous Intrafold Injection for Unilateral Vocal Fold Paralysis: Functional Results," *Ann. Otol. Rhinol Laryngol.*, 99(8):598-604 (Aug. 1990).

Horak et al., "Hydrogels in endovascular embolization. I. Spherical particles of poly (2-hydroxyethyl methacrylate) and their medico-biological properties", *Biomaterials*, 7(3):188-192 (May 1986).

Horak et al., "Hydrogels in endovascular embolization. II. Clinical use of spherical particles", *Biomaterials*, 7(6):467-470 (Nov. 1986).

Huang, et al., "Percutaneous endovascular embolization of intracerebral arteriovenous malformations. Experience in 72 cases", *Chin Med J*, vol. 108, No. 6, pp. 413-419, 1995.

"Injectable Tissue Implant Could Repair Ravages of Surgery", Clemson University, Biotech Week, Oct. 22, 2003, p. 117.

Jack, et al., "Radiolabeled polyvinyl alcohol particles: a potential agent to monitor embolization procedures", *Int J Rad Appl Instrum B*, vol. 13, No. 3, pp. 235-243, 1986.

Jiaqi, Y. et al., "A New Embolic Material: Super Absorbent Polymer (SAP) Microsphere and Its Embolic Effects," *Nippon Acta Radiologica*, 56:19-24 (1996) (English Abstract included).

Jones, S.K. et al., "Experimental Examination of a Targeted Hyperthermia System Using Inductively Heated Ferromagnetic Microspheres in Rabbit Kidney", *Phys. Med. Biol.*, vol. 46, No. 2, pp. 385-398, Feb. 2001, www.iop.org/Journals/pb.

Joy C, et al., "Use of Preoperative Embolization in the Treatment of Vascular Metastatic Lesions of the Spine," http://www.aaos.org/wordhtml/anmeet91/scipro/ppr472.htm, Mar. 12, 1991.

Jung et al., "Sulfobutylated poly(vinyl alcohol)-graft-poly(lactide-co-glycolide)s facilitate the preparation of small negatively charged biodegradable nanospheres," *Journal of Controlled Release*, 67:157-169 (2000).

Kai, et al., "The utility of the microcrystalline cellulose sphere as a particulate embolic agent: an experimental study", *American Journal of Radiology*, vol. 21, No. 6, pp. 1160-1163, 2000.

Kallmes, D.F. et al., "In Vitro Proliferation and Adhesion of Basic Fibroblast Growth Factor-producing Fibroblasts on Platinum Coils", *Radiology*, vol. 206, No. 1, pp. 237-243, Jan. 1998.

Kan, et al., "In vivo microscopy of the liver after injection of lipiodol into the hepatic artery and portal vein in the rat", *Acta Radiologica*, vol. 30, pp. 419-425, 1989.

Kerber, C., "Balloon Catheter with a Calibrated Leak", *Radiology*, vol. 120, pp. 547-550, Sep. 1976.

Kerber et al., "Polyvinyl Alcohol Foam: Prepackaged Emboli for Therapeutic Embolization", *American Journal Roentgenol*, vol. 130, pp. 1193-1194, Jun. 1978.

Kerber, "Flow-Controlled Therapeutic Embolization: A Physiologic and Safe Technique", *AJR*, vol. 134, pp. 557-561, Mar. 1980.

Khankan et al., "Embolic Effects of Superabsorbent Polymer Microspheres in Rabbit Renal Model: Comparison with Tris-acryl Gelatin Microspheres and Polyvinyl Alcohol," *Radiation Medicine*, 22(6):384-390 (2004).

Kim, et al., "Composite poly(vinyl alcohol) beads for controlled drug delivery", *Pharm Res*, vol. 9. No. 1, pp. 10-16, 1992.

Kim et al., "Hollow Silica Spheres of Controlled Size and Porosity by Sol-Gel Processing," *J. Am. Ceram. Soc.*, 74(8):1987-1992 (Aug. 1991).

Kim et al., "Poly(vinyl alcohol) beads with core-shell structure for drug delivery," *Cosmetic and Pharmaceutical Applications of Polymers*, Plenum Press, New York, pp. 209-214 (1991).

Kim et al., "Suspension polymerized poly(vinyl alcohol) beads for drug delivery," *Polymeric Materials: Science and Engineering, Proceedings of the ACS Division of Polymeric Materials: Science and Engineering*, 63:64-67 (1990).

Kochan, J.P. et al., "Interventional Neuroradiology: Current Practices and Techniques at Temple University Hospital," http://www.temple.edu/radiology/stroke.html, 5 pages.

Krinick et al., "A polymeric drug delivery system for the simultaneous delivery of drugs activatable by enzymes and/or light," *J. Biomater. Sci. Polymer Edn*, 5(4):303-324 (1994).

Kuhn, R. et al., "Embolic Occlusion of the Blood Supply to Uterine Myomas: Report of 2 Cases", *Aust. NZ. J. Obstet. Gynaecol.*, vol. 39, No. 1, pp. 120-122, Feb. 1999.

Kurata, et al., "Preoperative embolization for meningiomas using PVA particles", *No Shinkei Geka*, vol. 20, No. 4, pp. 367-373, 1992 (English Abstract included).

Kurbatova, G.T. et al., "Magnetically-guided Anesthetics Based on Highly Dispersed Iron Powders Coated by Polyacrylamide", *Biofizika*, vol. 47, No. 2, pp. 331-337, Mar.-Apr. 2002 http://intapp.medscape.com/px/medlineapp (English Abstract included).

Kurosaki et al., "Evaluation of PVA-Gel Spheres as GI-Transit Time Controlling Oral Drug Delivery System", *Proceedings of the 19th International Symposium on Controlled Release of Bioactive Materials*, Orlando, Florida, pp. 273-274, Jul. 26-31, 1992.

Kusano, et al., "Low-dose particulate polyvinylalcohol embolization in massive small artery intenstinal hemorrahage. Experimental and clinical results", *Invest Radiol*, vol. 22, No. 5, pp. 388-392, 1987.

Labarre et al., "Complement activation by substituted polyacrylamide hydrogels for embolisation and implantation", *Biomaterials*, vol. 23, pp. 2319-2327, 2002.

Lammer, et al., "Transcatheteral embolization with polyvinyl alcohol—technic and experimental studies", *Rontgenblatter*, vol. 36, No. 1, pp. 10-14, 1983 (English Abstract included).

Latchaw et al., "Polyvinyl Foam Embolization of Vascular and Neoplastic Lesions of the Head, Neck, and Spine", *Radiology*, vol. 131, pp. 669-679, Jun. 1979.

Laurent, "Materials and biomaterials for interventional radiology," *Biomed. & Pharmacother.*, 52:76-88 (1998).

Lemperle et al., "PMMA Microspheres for Intradermal Implantation: Part I. Animal Research," *Annals of Plastic Surgery*, 26(1):56-63 (Jan. 1991).

Lendlein, A. et al., "Biodegradable, Elastic Shape-Memory Polymers for Potential Biomedical Applications", *Science*, vol. 296, pp. 1673-1676, May 31, 2002.

(56) References Cited

OTHER PUBLICATIONS

Leung et al., "Determinants of Postembolization Syndrome after Hepatic Chemoembolization", *Journal of Vascular and Interventional Radiology*, vol. 12, No. 3, pp. 320-326, Mar. 2001.
Leventon, William, "Hemocompatible Coatings for Blood-Contacting Devices", *Medical Device & Diagnostic Industry: Coating Technologies—New Methods to Ensure Blood Compatibility*, vol. 25, No. 8, pp. 62-67, Aug. 2003.
Levy et al., "Transcatheter Uterine Artery Embolization for the Treatment of Symptomatic Uterine Fibroid Tumors," *Journal of Women's Imaging*, 2(4):168-175 (2000).
Lipman, "Uterine artery embolization for the treatment of symptomatic uterine fibroids: A review," *Applied Radiology*, 29(7):15-20 (Jul. 2000).
Lowery, C.L. et al., "Screening Tests for Intrauterine Growth Retardation: A Comparison of Umbilical Artery Doppler to Real-Time Ultrasound", *Echocardiography*, vol. 7, No. 2, pp. 159-164, Mar. 1990.
Marich, K.W. et al., "Real-Time Imaging with a New Ultrasonic Camera: Part I, In Vitro Experimental Studies on Transmission Imaging of Biological Structures", *Journal of Clinical Ultrasound*, vol. 3, No. 1, pp. 5-16, Mar. 1975.
Markoff, et al., "Uterine arteriovenous malformation successfully embolized with a liquid polymer, isobutyl 2-cyanoacrylate", *Am. J. Obstet. Gynecol.*, 155:659-660 (Sep. 1986).
Markus et al., "Experimental Aspects of High-Intensity Transient Signals in the Detection of Emboli," *J. Clin. Ultrasound.*, 23(2):81-87 (Feb. 1995).
Maruhashi, "Modified Polyvinyl Alcohols I and II," *Polyvinyl Alcohol—Developments*, John Wiley & Sons, Chichester, England, pp. 160-161 and pp. 186-191 (1992).
Marx, W. F. et al., "Endovascular Treatment of Experimental Aneurysms by Use of Biologically Modified Embolic Devices: Coil-mediated Intraaneurysmal Delivery of Fibroblast Tissue Allografts", *AJNR. Am. J. Neuroradiol.*, vol. 22, pp. 323-333, Feb. 2001.
Mather, P.T., Research Group Homepage, Basic Goals and Methods, http://www.ims.uconn.edu/~mather, 4 pages.
Matsumaru, et al., "Embolic materials for endovascular treatment of cerebral lesions", *J Biomater Sci Polym Ed*, vol. 8, No. 7, pp. 555-569, 1997.
Matsumoto, H. et al., "Basic Fibroblast Growth Factor Released from a Platinum Coil with a Polyvinyl Alcohol Core Enhances Cellular Proliferation and Vascular Wall Thickness: An In Vitro and In Vivo Study", *Neurosurgery*, vol. 53, No. 2, pp. 402-408, Aug. 2003.
Matsumoto, Y. et al., "Room-Temperature Ferromagnetism in Transparent Transition Metal-Doped Titanium Dioxide", *Science*, vol. 291, pp. 854-856, Feb. 2, 2001 www.sciencemag.org.
Mavligit, G. et al., "Gastrointestinal Leiomyosarcoma Metastatic to the Liver," *Cancer*, 75(8):2083-2088 (Apr. 15, 1995).
McIvor, J. et al., "Pregnancy After Uterine Artery Embolization to Control Haemorrhage from Gestational Trophoblastic Tumour", *British Journal of Radiology*, vol. 69, No. 823, pp. 624-629, Jul. 1996.
MerocelXL Sponge with Hytrol http://www.xomed.com/newproducts/merocelxl/merocelx1_earwick.asp, 3 pages, 2001.
Mid-America Interventional Radiological Society, "New Treatment for Uterine Fibroids Avoids Surgery," http://www.mirs.org/fibroids.htm, 6 pages, Submitted in Oct. 1999.
Moroz, P. et al., "Arterial Embolization Hyperthermia in Porcine Renal Tissue", *Journal of Surgical Research*, vol. 105, No. 2, pp. 209-214, Jun. 15, 2002.
Moroz, P. et al., "Hepatic Clearance of Arterially Infused Ferromagnetic Particles", *Int. J. Hyperthermia*, vol. 19, No. 1, pp. 23-24, Feb. 2003, http://www.tandf.co.uk/journals.
Nakabayashi, et al., "Evaluation of particulate embolic materials with MR imaging, scanning electron microscopy, and phase-contrast microscopy", *American Journal of Neuroradiology*, vol. 18, No. 3, pp. 485-491, 1997.
Nakstad, et al., "Embolization of intracranial arteriovenous malformations and fistulas with polyvinyl alcohol particles and platinum fibre coils", *Neuroradiology*, vol. 34, No. 4, pp. 348-351, 1992.
Namiki, "Application of Teflon Paste for Urinary Incontinence—Report of 2 Cases," *Uro. Int.*, 39:280-282 (1984).
Nash, et al., "Modifications of polystyrenic matrices for the purification of proteins. II. Effect of the degree of glutaraldehyde-poly(vinyl alcohol) crosslinking on various dye ligand chromatography systems", *J Chromatogr A*, vol. 776, No. 1, pp. 55-63, 1997.
Nikishin LF et al., "Interventional radiology in diffuse toxic goiter", *European Congress of Radiology*, Abstract 9041, 1999, http://www.ecr.org/conferences/ecr1999/sciprg/abs/p090041.htm, 7 pages.
Ophir, et al., "Ultrasonic backscatter from contrast producing collagen microspheres", *Ultrasonic Imaging*, vol. 2, pp. 67-77, 1980.
Oregon Health Sciences University, "Fibroid Embolization," http://www.uhmc.edu/dotter-fibroid, 34 pages.
Orienti et al., "Crosslinked Polyvinylalcohol Hydrogels as Vehicles for Hydrophilic Drugs," *Arch. Pharm. Pharm. Med. Chem.*, 333:421-424 (2000).
Orsini, L. F. et al., "Pelvic Organs in Premenarcheal Girls: Real-Time Ultrasonography", *Radiology*, vol. 153, No. 1, pp. 113-116, Oct. 1984.
Parker, et al., "A particulate contrast agent with potential for ultrasound imaging of liver", *Ultrasound in Medicine and Biology*, vol. 13, No. 9, pp. 555-566, 1987.
Pedley et al., "Hydrogels in Biomedical Applications," *British Polymer Journal*, 12:99-110 (Sep. 1980).
Pesant A.C. et al., "Dural fistulas involving the cavernous sinus: Treatment by embolization—7 cases", *European Congress of Radiology*, Abstract 3-088, 1997, http://www.ecr.org/conferences/ecr1997/sciprg/abs/9703088p.htm, 1 page.
Phillips, D. R. et al., "Experience with Laparoscopic Leiomyoma Coagulation and Concomitant Operative Hysteroscopy", *J. Am. Assoc. Gynecol. Laparosc*, vol. 4, No. 4, pp. 425-533, Aug. 1997.
Physicians' Desk Reference Family Guide to Women's Health, "Chapter 7—Common Disorders of the Reproductive System," http://www.healthsquare.com/pdrfg/wh/chapters/wh1ch01.htm, 24 pages.
Pistel et al., "Brush-like branched biodegradable polyesters, part III Protein release from microspheres of poly(vinyl alcohol)-graft-poly(D,L-lactic-co-glycolic acid)," *Journal of Controlled Release*, 73:7-20 (2001).
Politano et al., "Periurethral Teflon Injection for Urinary Incontinence," *The Journal of Urology*, 111:180-183 (1974).
Poppe, W. et al., "Pregnancy after Transcatheter Embolization of a Uterine Arteriovenous Malformation", *Am. J. Obstet. Gynecol.*, vol. 156, No. 5, pp. 1179-1180, May 1987.
Pritchard, et al., "Poly(Vinyl Alcohol): Basic Properties and Uses", London, England: Gordon and Breach Science Publishers, pp. 95-97, 1970.
Progelhof et al., "Table 4.21. Properties of electrical insulating films (101)," *Polymer Engineering Principles: Properties, Processes, and Tests for Design*, Hanser Publishers, Munich, p. 383 (1993).
Pryor J. and Berenstein A., "Epistaxis (Nose-bleeds)," http://www.wehealny.org/inn/Radiology/nosebleeds.html, 1 page.
"Pulmonary artery pseudoaneurysm/aneurysm," http://www.mamc.amedd.army.mil/williams/chest/vascular/paaneurysm/paaneyrysm.htm, 2 pages.
Purdy, et al., "Arteriovenous malformations of the brain: choosing embolic materials to enhance safety and ease of excision", *J Neurosurg*, vol. 77, No. 2, pp. 217-222, 1992.
PVA Plus, AngioDynamics® Inc., "Reliable PVA Foam Formulated for Consistency and Controlled Delivery—Embolization Particles Ordering Information," www.angiodynamics.com, 2 pages (Aug. 2002).
Quisling, et al., "Histopathology analysis of intraarterial polyvinyl alcohol microemboli in rat cerebral cortex", *American Journal of Neuroradiology*, vol. 5, pp. 101-104, 1984.
Rajan et al., "Sarcomas Metastatic to the Liver: Response and Survial after Cisplatin, Doxorubicin, Mitomycin-C, Ethiodol, and Polyvinyl Alcohol Chemoembolization", *Journal of Vascular and Interventional Radiology*, vol. 12, No. 2, pp. 187-193, Feb. 2001.

(56) References Cited

OTHER PUBLICATIONS

Ramos, et al., "Tumor vascular signals in renal masses: detection with Doppler US", *Radiology*, vol. 168, No. 3, pp. 633-637, 1988.
Ravina, J.H. et al., "Advantage of Pre-Operative Embolization of Fibroids: About a Multicentric Set of 31 Cases", *Contracept. Fertil. Sex.*, vol. 23, No. 1, pp. 45-49, Jan. 1995 (English Abstract included).
Ravina, J.H. et al., "Arterial Embolisation to Treat Uterine Myomata", *Lancet*, vol. 346, pp. 671-674, Sep. 9, 1995.
Ravina, J.H. et al., "Interest of Particulate Arterial Embolization in the Treatment of Some Uterine Myoma", *Bull. Acad. Natle. Med.*, vol. 181, No. 2, pp. 233-246, Feb. 4, 1997 (English Summary included).
Repa, I. et al., "Mortalities Associated with Use of a Commercial Suspension of Polyvinyl Alcohol," *Radiology*, 170(2):395-399 (Feb. 1989).
Rhine et al., "Polymers for Sustained Macromolecule Release: Procedures to Fabricate Reproducible Delivery Systems and Control Release Kinetics," *Journal of Pharmaceutical Sciences*, 69(3):265-270 (Mar. 1980).
Rump, A. et al., "Pharmacokinetics of Intraarterial Mitomycin C in the Chemoembolisation Treatment of Liver Metastases," *Gen. Pharmac.*, 27(4):669-671 (1996).
Schetky, "Shape-Memory Alloys," *Encyclopedia of Chemical Technology*, Third Edition, vol. 20, John Wiley & Sons, New York, pp. 726-736 (1982).
Schlief, R. et al., "Enhanced Color Doppler Echocardiography of the Left Heart After Intravenous Injection of a New Saccharide Based Agent in Humans", *Circulation*, vol. 82, No. 2, p. 28, Oct. 1990 (Abstract).
Schlief, R. et al., "Successful Opacification of the Left Heart Chamber on Echocardiographic Examination after Intravenous Injection of a New Saccharide Based Contrast Agent", *Echocardiography*, vol. 7, No. 1, pp. 61-64, Jan. 1990.
Schwarz et al., "The acoustic filter: An ultrasonic blood filter for the heart-lung machine," *J. Thorac. Cardiovasc. Surg.*, 104(6):1647-1653 (Dec. 1992).
Shafik, "Intraesophageal Polytef injection for the treatment of reflux esophagitis," *Surg. Endosc.*, 10:329-331 (1996).
Shape Shifters, http://www.sciam.com/tehbiz/0501scicit6.html, 3 pages, 2001.
Shung, K.K. et al., "Scattering of Ultrasound by Blood", *IEEE Transactions on Biomedical Engineering*, vol. BME-23, No. 6, pp. 460-467, Nov. 1976.
Sigelmann, R.A. et al., "Analysis and Measurement of Ultrasound Backscattering from an Ensemble of Scatters Excited by Sine-Wave Bursts", *Journal of Acoustical Society of America*, vol. 53, No. 4, pp. 1351-1355, Apr. 1973.
SIR-Spheres (Yttrium-90 Microspheres), pp. 1-12.
SIR-Spheres, Radioactive Implant (Yttrium-90 Microspheres), Sirex Medical, Inc., San Diego, CA, Nov. 6, 2000, pp. 1-15.
Sirtex Medical Limited—Product Description http://www.sirtex.com/?p=72, 3 pages (Retrieved from the internet on May 27, 2003).
Sirtex Medical Limited—Targeted Radiotherapy with SIR-Spheres http://www.sirtex.com/?p=57, 2 pages (Retrieved from the internet on May 27, 2003).
Siskin et al., "Pathologic Evaluation of a Spherical Polyvinyl Alcohol Embolic Agent in a Porcine Renal Model," *J. Vasc. Interv. Radiol.*, 14:89-98 (2003).
Skotland, T. et al., "In Vitro Stability Analyses as a Model for Metabolism of Ferromagnetic Particles (Clariscan™), a Contrast Agent for Magnetic Resonance Imaging", *J. Pharm. Biomed. Anal.*, vol. 28, No. 2, pp. 323-329, Apr. 15, 2002.
"Smart Sutures Tie Themselves", Apr. 26, 2002, http://www.sciam.com/article.cfm?articleID=00047706-121F-1CD0-B4A8809EC588, 2 pages.
Smith et al., "Evaluation of Polydimethylsiloxane as an alternative in the Endoscopic Treatment of Vesicoureteral Reflux," *The Journal of Urology*, 152:1221-1224 (Oct. 1994).

Smith et al., "Left Heart Opacification with Peripheral Venous Injection of a New Saccharide Echo Contrast Agent in Dogs", *JACC*, vol. 13, No. 7, pp. 1622-1628, Jun. 1989.
Soppimath et al., "Controlled release of antihypertensive drug from the interpenetrating network poly(vinyl alcohol)-guar gum hydrogel microspheres," *J. Biomater. Sci. Polymer Edn*, 11(1):27-43 (2000).
Spickler, et al., "The MR appearance of endovascular embolic agents in vitro with clinical correlation", *Comput Med Imaging Graph*, vol. 14, No. 6, pp. 415-423, 1990.
Spies JB, "Georgetown University Medical Center. Uterine Fibroid Embolization (UFE). An alternative to surgery for patients with uterine fibroids. Literature Review," http://www.fibroidoptions.com/pr-lit.htm, 6 pages, Sep. 1, 2001.
Stancato-Pasik, A. et al., "Obstetric Embolotherapy: Effect on Menses and Pregnancy", *Radiology*, vol. 204, No. 3, pp. 791-793, Sep. 1997.
Stein, R. et al., "Targeting Human Cancer Xenografts with Monoclonal Antibodies Labeled Using Radioiodinated, Diethylenetriaminepentaacetic Acid-appended Peptides", *Clinical Cancer Research*, vol. 5, No. 10, pp. 3079-3087, Oct. 1999 (Supplement).
Strasnick et al., "Transcutaneous Teflon® Injection for Unilateral Vocal Cord Paralysis: An Update," *The Laryngoscope*, 101:785-787 (Jul. 1991).
Stridbeck, H. et al, "Collateral Circulation Following Repeated Distal Embolization of the Hepatic Artery in Pigs," *Invest. Radiol.*, 19(3):179-183 (1984).
Strunk, et al., "Treatment of congenital coronary arteriovenous malformations with microparticle embolization", *Cathet Cardiovasc Diagn*, vol. 22, No. 2, pp. 133-136, 1991.
Swanson DA et al., "The role of embolization and nephrectomy in the treatment of metastatic renal carcinoma", *Urologic Clinics of North America*, 7(3):719-730, 1980. University of Pennsylvania Cancer Center—Oncolink, http://www.oncolink.upenn.edu/pdg_html/cites/00/00585.html.
Tabata et al., "Tumor accumulation of poly(vinyl alcohol) of different sizes after intravenous injection", *Journal of Controlled Release*, vol. 50, pp. 123-133, Jan. 2, 1998.
Tadavarthy et al., "Polyvinyl Alcohol (Ivalon)—A New Embolic Material", *The American Journal of Roentgenology Radium Therapy and Nuclear Medicine*, vol. 125, No. 3, pp. 609-616, Nov. 1975.
Tadavarthy et al., "Polyvinyl Alcohol (Ivalon) as an Embolizing Agent", *Seminars in Interventional Radiology*, vol. 1, No. 2, pp. 101-109, Jun. 1984.
Tamatani, S. et al., "Histological Interaction of Cultured Endothelial Cells and Endovascular Embolic Materials Coated with Extracellular Matrix", *J. Neurosurg.*, vol. 86, No. 1, pp. 109-112, Jan. 1997.
Tao, et al., "Study of microspheres for embolization of hepatic artery", *Acta Pharmaceutica Sinica*, vol. 23, No. 1, pp. 55-60, 1988.
Tao, et al., "Study of microspheres for embolization of hepatic artery", (Translation) *Acta Pharmaceutica Sinica*, vol. 23, No. 1, pp. 55-60, 1988.
Terada, et al., "Preoperative embolization of meningiomas fed by ophthalmic branch arteries", *Surg Neurol*, vol. 45, No. 2, pp. 161-166, 1996.
Thanoo, et al., "Controlled release of oral drugs from cross-linked polyvinyl alcohol microspheres", *J Pharm Pharmacol*, vol. 45, No. 1, pp. 16-20, 1993.
Thanoo, B. C. et al., "Preparation and Properties of Barium Sulphate and Methyl Iothalamate Loaded Poly(vinyl Alcohol) Microspheres as Radiopaque Particulate Emboli," *Journal of Applied Biomaterials*, 2:67-72 (1991).
Thanoo, et al., "Tantalum loaded silicone micropsheres as particulate emboli", *J Microencapsul*, vol. 8, No. 1, pp. 95-101, 1991.
Thelen, V.M. et al., "Catheter Embolisation of Metastasising Renal Carcinomas Using Butyle-2-cyano-acrylate", *Fortschr. Rontgenstr.*, vol. 124, No. 3, pp. 232-235, Mar. 1976 (English Abstract included).
The Fibroid Embolization Center of the New York United Hospital Medical Center, "Fibroid Facts," http://www.uhmc.com/fibro2.htm, 9 pages.

(56) References Cited

OTHER PUBLICATIONS

The Vanderbilt-Ingram Cancer Center, "Kidney Cancer," http://www.mc.Vanderbilt.Edu/cancer/cancerinfo/kidney.html, 1 page, 2001.
Tian et al., "Design and synthesis of amphiphilic poly (ethylene glycol) derivatives as micellar drug delivery systems," *Polymer Preprints*, 43(2):719-720 (Fall 2002).
Tikkakoski, et al., "Preoperative embolization in the management of neck paragangliomas", *Laryngoscope*, vol. 107, pp. 821-826, 1997.
Toon, "Improving a Key Weapon Against Cancer," Research Horizons, pp. 11-12, Spring/Summer 2001.
Touho, et al., "Intravascular treatment of spinal arteriovenous malformations using a microcatheter—with special reference to serial xylocaine tests and intravascular pressure monitoring", *Surgical Neurology*, vol. 42, No. 2, pp. 148-156, 1994.
UCLA Radiological Sciences, "A summary of terms appearing in this text," http://www.radsci.ucla.edu:8000/aneurysm/terms.html, 1 page.
University Medical Center SUNY Stony Brook, Department of Urology, "Variococele and its treatment," http://www.hsc.sunysb.edu/urology/male_inf...variocoele_and_its_treatment.html, 8 pages, Last Updated on Mar. 12, 2001.
Vivas S et al., "Arterioportal fistula and hemobilia in a patient with hepatic transplant", Gastroenterol Hepatol, 21(2):88-9, http://www.doyma.es/copiani/revistas/gastro/abstr/abs_p080.html, Feb. 1998 (English Abstract included).
Vogel F, "Nonsurgical Management of Uterine Fibroids," http://www.holyname.org/brochure/fibroids.html, 5 pages.
Wakhloo, et al., "Extended preoperative polyvinyl alcohol microembolization of intracranial meningiomas: Assessment of two embolization techniques", *American Journal of Neuroradiology*, vol. 14, pp. 571-582, 1993.
Walker WJ, "Non Surgical Treatment of Fibroids in the UK by Uterine Artery Embolisation—An Alternative to Hysterectomy, Myomectomy and Myolysis," http://www.fibroids.co.uk/thepaper.html, 2 pages, 2002.
Walsh RM et al., "Role of Angiography and Embolization for Acute Massive Upper Gastronintestinal Hemorrhage," *J. Gastrointest. Surg.*, 3:61-66 (1999).
Waltman, A.C. et al., "Technique for Left Gastric Artery Catheterization", *Radiology*, vol. 109, No. 3, pp. 732-734, Dec. 1973.
White, Jr., "Embolotherapy in Vascular Disease," *American Journal of Roentgenology*, 142:27-30 (Jan. 1984).
Widder, K.J. et al., "Selective Targeting of Magnetic Microspheres Containing Adriamycin: Total Remission in Yoshida Sarcoma-Bearing Rats", *Proceedings of the 16th Annual Meeting of American Society of Clinical Oncology*, May 26-27, 1980, San Diego, CA, p. 261.
Widder, K. et al., "Magnetic Microspheres: Synthesis of a Novel Parenteral Drug Carrier", *Journal of Pharmaceutical Sciences*, vol. 68, No. 1, pp. 79-82, Jan. 1979.
Wikholm G et al., "Embolization of Cerebral Arteriovenous Malformations: Part I—Technique, Morphology, and Complications", *Neurosurgery*, 39(3):448-459 (Sep. 1996).
Winters et al., "Periurethral injection of collagen in the treatment of intrinsic sphincteric deficiency in the female patient," *The Urologic Clinics of North America*, 22(3):673-678 (Aug. 1995).
Worthington-Kirsch RL, "Interventionalists offer management option for uterine fibroids," *Diagnostic Imaging*, 21(3):47-49, Mar. 1999, http://www.dimag.com/references/9903wortrefs.html.
Worthington-Kirsch, et al., "Uterine arterial embolization for the management of leiomyomas: Quality-of-life assessment and clinical response", *Radiology*, vol. 208, No. 3, 625-629, 1998.
Wright, K.C. et al., "Partial Splenic Embolization Using Polyvinyl Alcohol Foam, Dextran, Polystyrene, or Silicone," *Radiology*, 142:351-354, Feb. 1982.
Wu, A.M., "Engineered Antibodies for Breast Cancer Imaging and Therapy," http://www.cbcrp.org/research/PageGrant.asp?grant_id=111, 3 pages, 1996.
Yamada, T. et al., "Extended Intraarterial Cisplatin Infusion for Treatment of Gynecologic Cancer After Altercation of Intrapelvic Blood Flow and Implantation of a Vascular Access Device", *Cardiovasc. Intervent. Radiol.*, vol. 19, pp. 139-145, 1996.
Yamashita, Y. et al., "Transcatheter Arterial Embolization of Obstetric and Gynaecological Bleeding: Efficacy and Clinical Outcome", *British Journal of Radiology*, vol. 67, pp. 530-534, Jun. 1994.
Yoon et al., "Surface Immobilization of Galactose onto Aliphatic Biodegradable Polymers for Hepatocyte Culture," *Biotechnol. Bioeng.*, 78(1):1-10 (Apr. 5, 2002).
Yusi et al., "Submuscosal Injection of Polyvinyl Alcohol in Artificially Created Vesico-Ureteral Reflux: A Preliminary Report," *Asian J. Surg.*, 18(2):122-127 (Apr. 1995).
Zisch et al., "Covalently conjugated VEGF-fibrin matrices for endothelialization," *Journal of Controlled Release*, 72:101-113 (2001).
Ziskin, M.C. et al., "Contrast Agents for Diagnostic Ultrasound", *Investigative Radiology*, vol. 7, No. 6, pp. 500-505, Nov.-Dec. 1972.
Zou, Ying-hua, et al. "Experimental Canine Hapatic Artery Embolization with Polyvinyl Alcohol Microspheres," *Zhong Hua Fang-She Xue ZaZhi*, 23(6):330-332 (1989).
Zou, Ying-hua, et al. "Experimental Canine Hapatic Artery Embolization with Polyvinyl Alcohol Microspheres," Translation, *Zhong Hua Fang-She Xue ZaZhi*, 23(6):330-332 (1989).

\* cited by examiner

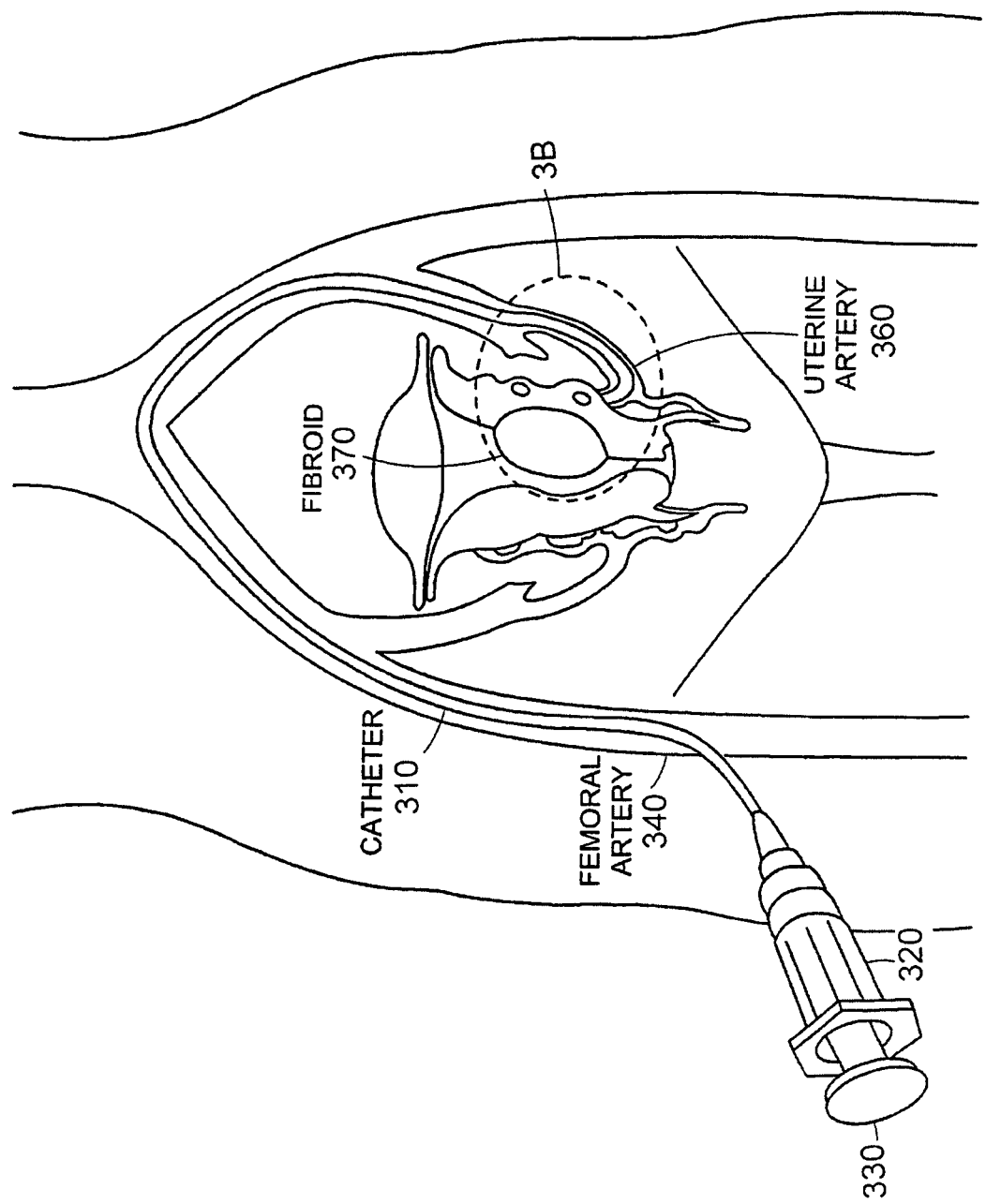

METHODS AND SYSTEMS FOR COATING PARTICLES

TECHNICAL FIELD

This invention relates to methods and systems for coating particles.

BACKGROUND

Therapeutic vascular occlusions (embolizations) can be used to prevent or treat pathological conditions in situ. Compositions including embolic particles can be used for occluding vessels in a variety of medical applications. Delivery of embolic particles through a catheter is dependent on size uniformity, density and compressibility of the embolic particles.

SUMMARY

The invention relates to methods and systems for coating particles.

In one aspect of the invention, a method includes passing a particle through a container containing a coating material so that the particle becomes at least partially coated with the coating material. The particle has a diameter of about 3,000 microns or less.

In another aspect of the invention, a method includes flowing multiple particles through a container containing a coating material so that each of the multiple particles is at least partially coated with the coating material. The multiple particles have an arithmetic mean diameter of about 3,000 microns or less. The method further includes forming the at least partially coated particles into a stream of the at least partially coated particles.

In a further aspect of the invention, a method includes forming a discontinuous stream of a coating material. The discontinuous stream includes multiple discrete portions of the coating material. The method further includes disposing a particle in at least one of the discrete portions of the coating material. The particle has a diameter of about 3,000 microns or less.

In an additional aspect of the invention, a system includes a tube having an inner diameter of about 3,500 microns or less, a flow control mechanism configured to force a continuous stream of material through the tube, and an energy injection device configured to form the continuous stream into a discontinuous stream. The discontinuous stream includes at least one discrete portion of the material.

Embodiments may include one or more of the following features.

In some embodiments, the method further includes passing multiple particles through the container so that each of the multiple particles become at least partially coated with the coating material, and the multiple particles have an arithmetic mean diameter of about 3,000 microns or less.

In certain embodiments, the multiple particles that are at least partially coated with the coating material are in the form of a stream.

In some embodiments, the stream is a continuous stream of the multiple at least partially coated particles.

In certain embodiments, the method further includes forming the continuous stream of the multiple at least partially coated particles into a discontinuous stream of at least partially coated particles.

In some embodiments, the continuous stream of the multiple at least partially coated particles is formed into the discontinuous stream of at least partially coated particles outside the container.

In certain embodiments, the stream is a discontinuous stream of the multiple at least partially coated particles.

In some embodiments, forming the stream includes flowing the particles through a first orifice and flowing the coating material through a second orifice. The first orifice is concentrically disposed within the second orifice.

In certain embodiments, the coating material that at least partially coats the multiple particles includes a gelling precursor.

In some embodiments, the method further includes forming the gelling precursor into a gel.

In certain embodiments, forming the gel includes contacting the gelling precursor with a gelling agent.

In some embodiments, the gelling agent includes calcium chloride.

In certain embodiments, the method further includes detecting a position of the particles within the stream, and separating a first portion of the stream from a second portion of the stream as a function of the detected position of the particles.

In some embodiments, the coating material that at least partially coats the particle includes a gelling precursor.

In certain embodiments, the method further includes forming the gelling precursor that at least partially coats the particle into a gel.

In some embodiments, forming the gel includes contacting the gelling precursor that at least partially coats the particle with a gelling agent.

In certain embodiments, the gelling agent includes calcium chloride.

In some embodiments, the particle includes polyvinyl alcohol.

In certain embodiments, the coating material includes a gelling precursor.

In some embodiments, the gelling precursor includes sodium alginate.

In certain embodiments, the coating material includes a therapeutic agent.

In some embodiments, the coating material includes a composition of a gelling precursor and a therapeutic agent.

In certain embodiments, the method further includes forming a liquid containing the coating material and the particle, and disposing the liquid in the container.

In some embodiments, disposing the liquid in the container includes applying pressure to the liquid.

In certain embodiments, the method further includes flowing the liquid through the container.

In some embodiments, the method further includes disposing a liquid containing the coating material in the container, and after disposing the liquid in the container, disposing the particle in the container.

In certain embodiments, disposing the liquid in the container includes applying pressure to the liquid.

In some embodiments, the method further includes flowing the liquid through the container.

In certain embodiments, the particle has a diameter of about 10 microns or more.

In some embodiments, the container is in the shape of a tube.

In certain embodiments, the discontinuous stream of the multiple at least partially coated particles includes exposing the container to energy.

In some embodiments, the energy is in the form of energy pulses.

In certain embodiments, the energy is vibrational energy, laser light, and/or gas pulses.

In some embodiments, forming the discontinuous stream of the multiple at least partially coated particles includes injecting pulses of a gas into the continuous stream of the multiple at least partially coated particles.

In some embodiments, the method further includes forming the coating material that at least partially coats the particles in the stream into a gel.

In certain embodiments, the method further includes disposing at least one particle in each of at least some of the multiple discrete portions of the coating material.

In some embodiments, the method further includes forming the discrete portions of the coating material into a gel.

In certain embodiments, the material includes a coating material.

In some embodiments, the system further includes a particle introducing device configured to introduce a particle into the at least one discrete portion so that the coating material of the at least one discrete portion at least partially surrounds the particle.

In certain embodiments, the system further includes a sensing device adapted to detect a position of the at least one particle within the tube. The sensing device is in communication with the particle introducing device.

In some embodiments, the system further includes a container configured to receive the at least one portion after the at least one portion exits the tube.

In certain embodiments, the material includes a composition of a coating material and multiple particles, and the at least one discrete portion includes one of the particles at least partially surrounded by the coating material.

In some embodiments, the system further includes a sensing device adapted to detect a position of the multiple particles within the tube. The sensing device is in communication with the gas injection device.

In certain embodiments, the system further includes a container configured to receive the at least one portion after the at least one portion exits the tube.

Embodiments can include one or more of the following advantages.

In some embodiments, the methods help to ensure that individual particles, rather than agglomerations of particles, are coated. As a result, the size and shape of the coated particles can be better controlled. This, for example, can improve the results of various medical treatments in which the coated particles can be used.

In certain embodiments, the methods can allow the particles to be coated in a substantially continuous fashion. This can, for example, allow the particles to be coated relatively efficiently.

Other features and advantages can be found in the description, drawings, and claims.

DESCRIPTION OF DRAWINGS

FIG. 3A is a schematic illustrating injection of an embolic composition including embolic particles into a vessel.

FIG. 7A is a schematic of the manufacture of an embolic composition while

DETAILED DESCRIPTION

The invention relates to methods and systems for coating particles, such as particles having a diameter of about 3,000 microns or less. In general, the methods involve passing a particle through a container containing a coating material so that the particle becomes at least partially coated with the coating material. In some embodiments, the coating material that at least partially coats the particle is then be formed into a gel in order to form a gel-coated particle.

Figure 1:
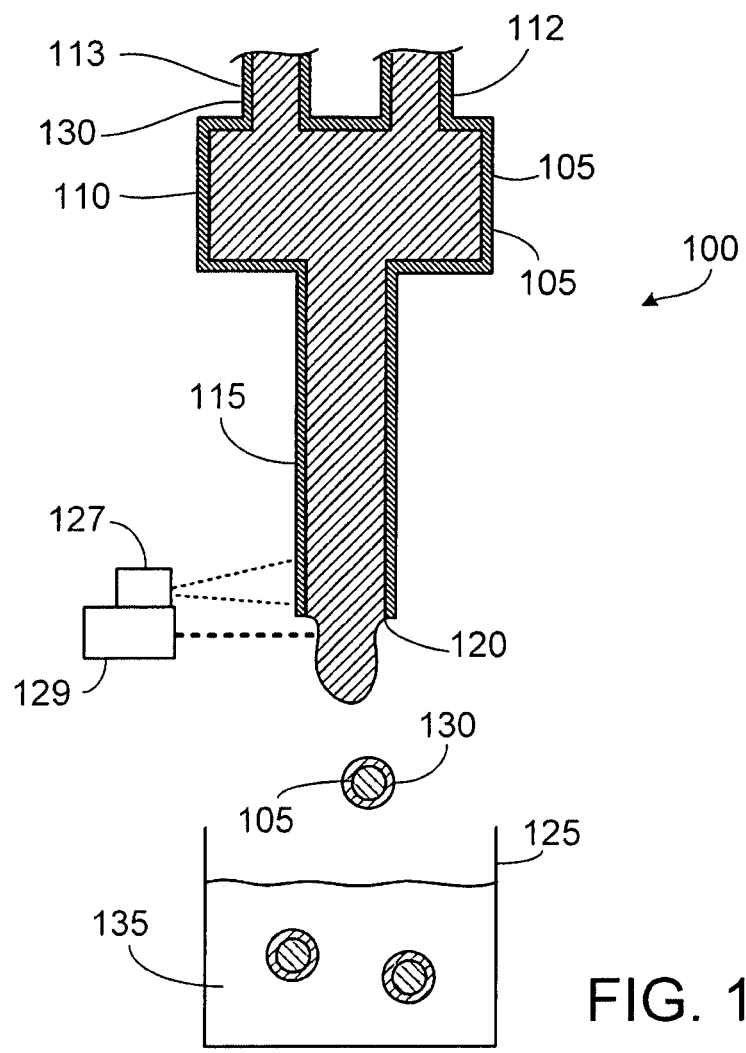
FIG. 1 is a cross-sectional view of an embodiment of a particle-coating system.

FIG. 1 shows a system 100 for coating particles. System 100 includes a pump 110 that is fluidly connected to a tube 115. Tube 115 defines an outlet 120 directed towards a reservoir 125, which contains a gelling agent 135 (e.g., calcium chloride). A sensing device 127 is positioned adjacent tube 115, and a separating device 129 is positioned in close proximity to outlet 120 of tube 115. Separating device 129 is in communication with sensing device 127, as described below.

Figure 2:
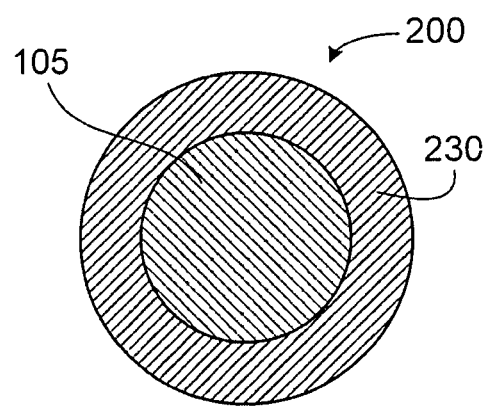
FIG. 2 is a cross-sectional view of an embodiment of a coated-particle.

During use, particles 105 (e.g., polyvinyl alcohol particles) and a coating material 130 (e.g., a mixture of a gelling precursor and a therapeutic agent) are introduced into pump 110 via inlets 112 and 113, respectively, to form a composition including particles 105 and coating material 130. The gelling precursor of coating material 130 can, for example, be sodium alginate, and the therapeutic agent of coating 130 can, for example, be TORADOL®. Pump 110 forces a stream of the composition of particles 105 and coating material 130 through tube 115 in the direction of outlet 120. As the stream passes through tube 115, sensing device 127 detects the location of particles 105 within the stream (e.g., within tube 115), and communicates that information to separating device 129 (e.g., a laser device). As the stream passes through outlet 120, separating device 129 is activated in order to direct laser energy (e.g., laser light) into the stream, causing a droplet, including one particle 105 surrounded by coating material 130, to be separated from the stream. In order to help ensure that separating device 129 separates droplets that include only one particle 105 from the stream at a time, separating device 129 can be controlled as a function of the detected location of particles 105 within the stream. For example, based on the information transferred from sensing device 127 to separating device 129 regarding the location of particles 105 within the stream, separating device 129 can be activated such that the energy (e.g., laser light) contacts those portions of the stream between adjacent particles 105 (e.g., those regions of the stream that include only coating material 130). As the droplets are separated from the remainder of the stream, the droplets are collected in reservoir 125 where coating material 130 (e.g., a gelling precursor of coating material 130), which surrounds individual particles 105, reacts with gelling agent 135 to form a gel coating surrounding particles 105, resulting in a particle 200 that includes a particle 105 surrounded by a gel 230 (FIG. 2). The therapeutic agent of coating material 130 is contained within the gel coating.

Pump 110 can be any of various high-pressure pumping devices. For example, pump 110 can be a syringe pump (e.g., model PHD4400, Harvard Apparatus, Holliston, Mass.). Alternatively or additionally, pump 110 can, for example, be an extruder pump, a piston pump, a vane pump, or a peristaltic pump. Generally, the force applied to the composition by pump 110 depends on the viscosity of the composition and/or the desired flow rate of the composition through tube 115.

While pump 110 has been described as forcing the composition of particles 105 and coating material 130 directly into tube 115, in some embodiments, one or more pumps can be arranged to force a stream of particles 105 and a stream of coating material 130 into a mixing chamber where they are mixed to form a composition that can then be fed through tube 115.

Due to the size of tube 115 relative to particles 105, particles 105 generally travel through tube 115 in a single file fashion. As a result, only one particle 105 is generally permitted to pass through outlet 120 of tube 115 at a time. In some embodiments, tube 115 has an inner diameter of about 3,500 microns or less (e.g., about 3,000 microns or less, about 2,500 microns or less, about 2,000 microns or less, about 1,500 microns or less, about 1,200 microns or less, about 1,000 microns or less, about 800 microns or less, about 600 microns or less, about 400 microns or less, about 200 microns or less) and/or an inner diameter of about 20 microns or more (e.g., about 100 microns or more, about 300 microns or more, about 400 microns or more, about 500 microns or more, about 700 microns or more, about 900 microns or more, about 1,000 microns or more, about 1,200 microns or more, about 1,500 microns or more, about 2,000 microns or more, about 2,500 microns or more, about 3,000 microns or more). In certain embodiments, tube 115 has an inner diameter of about 20 microns to about 3,000 microns (e.g., about 100 microns to about 1,200 microns).

In some embodiments, sensing device 127 is a light sensing device. Sensing device 127 can, for example, include a light emitter and a light detector, each positioned on a common side of tube 115. During use, light is emitted from the light emitter and directed toward tube 115 and/or the stream passing through tube 115, and the detector measures the amount of light reflected by tube 115 and/or the stream passing through tube 115. Based on the level of light detected by the detector, sensing device 127 can determine whether one or more particles 105 and/or coating material 130 is present within the region of the tube contacted by the light. Sensing device 127 can alternatively or additionally include a light emitter positioned on one side of tube 115 and a light sensor positioned on the opposite side of tube 115. During use, the light emitter can emit light through tube 115 and/or the stream passing through tube 115 and the light sensor can measure the amount of light that travels through tube 115 and or the steam passing through tube 115. Based on the amount of light detected by the sensor, it is possible for sensing device 127 to detect the presence of one or more particles 105 and/or coating material 130 in the region of tube 115 through which the light is directed.

While sensing device 127 has been described as a light sensing device, any of various other types of devices capable of detecting the location of particles 105 and/or coating material 130 as they pass through tube 115 can be used.

Separating device 129, as described above, can direct laser light into the stream shortly after the stream passes through outlet 120 in order to separate droplets from the composition of particles 105 and coating material 130 passing through tube 115. The laser light, for example, can interrupt a portion of coating material 130 between adjacent particles 105 in order to separate a droplet from the stream.

In certain embodiments, separating device 129 emits laser light (e.g., visible light, UV light, IR light, and/or near IR light). In some embodiments, separating device 129 is controlled as a function of the position of particles 105 (as detected by sensing device 127), the flow rate of the composition of particles 105 through tube 115, and/or the distance between separating device 129 and sensing device 127. The above-noted parameters can be used, for example, to determine the frequency with which separating device 129 is activated in order to help ensure that the laser light emitted from separating device 129 is directed to a region of the stream between adjacent particles 105 (e.g., a region of the stream including only coating material 130). Consequently, separating device 129 can be controlled to separate droplets including one particle 105 surrounded by coating material 130 from the stream.

While separating device 129 has been described above as a laser light emitting device, separating device 129 can alternatively or additionally be configured to emit any of various other forms of energy to form droplets from the stream of particles 105 and coating material 130. In some embodiments, separating device 129 is configured to direct a pulse of gas (e.g., air) into the stream in order to form the droplets. Separating device 129, for example, can be an air knife. In certain embodiments, separating device 129 is configured to impart vibrational energy to tube 115 and/or to the stream passing through tube 115. In such embodiments, separating device 129 can be a vibrating mechanism attached to tube 115 near outlet 120. The vibrational energy can cause droplets to separate from the stream as they pass through outlet 120. Any of these various types of separating devices can be in communication with sensing device 127 in order to help ensure that the formed droplets include only one particle 105.

In general, particles 105 can be any desired size or shape. In some embodiments, particles 105 have a diameter of about 3,000 microns or less (e.g., about 2,500 microns or less; about 2,000 microns or less; about 1,500 microns or less; about 1,200 microns or less; about 1,000 microns or less; about 900 microns or less; about 700 microns or less; about 500 microns or less; about 400 microns or less; about 300 microns or less; about 100 microns or less) and/or about ten microns or more (e.g., about 100 microns or more; about 300 microns or more; about 400 microns or more; about 500 microns or more; about 700 microns or more; about 900 microns or more; about 1,000 microns or more; about 1,200 microns or more; about 1,500 microns or more; about 2,000 microns or more; about 2,500 microns or more). In certain embodiments, particles 105 have a diameter of from about ten microns to about 3,000 microns (e.g., from about 40 microns to about 2,000 microns; from about 100 microns to about 700 microns; from about 500 microns to about 700 microns; from about 100 microns to about 500 microns; from about 100 microns to about 300 microns; from about 300 microns to about 500 microns; from about 500 microns to about 1,200 microns; from about 500 microns to about 700 microns; from about 700 microns to about 900 microns; from about 900 microns to about 1,200 microns).

The above-noted particle diameters can, for example, be arithmetic mean diameters of multiple particles 105. The arithmetic mean diameter of a group of particles can be determined using a Beckman Coulter RapidVUE Image Analyzer version 2.06 (Beckman Coulter, Miami, Fla.). The arithmetic mean diameter of a group of particles (e.g., in a composition) can be determined by dividing the sum of the diameters of all of the particles in the group by the number of particles in the group.

In certain embodiments, particles 105 are formed of one or more biocompatible material(s). In some embodiments, particles 105 are formed of one or more polymers. The weight average molecular weight of the polymer(s) with which particles 105 are formed can be in the range of from about 9,000 to about 186,000 (e.g., from about 85,000 to about 146,000, from about 89,000 to about 98,000). Examples of polymers from which particles 105 can be formed include polyvinyl alcohols, polyacrylic acids, polymethacrylic acids, poly vinyl sulfonates, carboxymethyl celluloses, hydroxyethyl celluloses, substituted celluloses, polyacrylamides, polyethylene glycols, polyamides, polyureas, polyurethanes, polyesters, polyethers, polystyrenes, polysaccharides, polylactic acids, polyethylenes, polymethylmethacrylates, polycaprolactones, polyglycolic acids, poly (lactic-co-glycolic) acids (e.g., poly(d-lactic-co-glycolic) acids) and copolymers or mixtures thereof.

Particles 105 can be formed using any of various methods, such as droplet generation techniques. Examples of suitable methods for forming particles 105 are described in U.S. Published Patent Application No. US 2004-0096662 A1 and in U.S. patent application Ser. No. 10/858,253, filed Jun. 1, 2004, both of which are incorporated by reference herein.

Manufacture

Figure 7A:
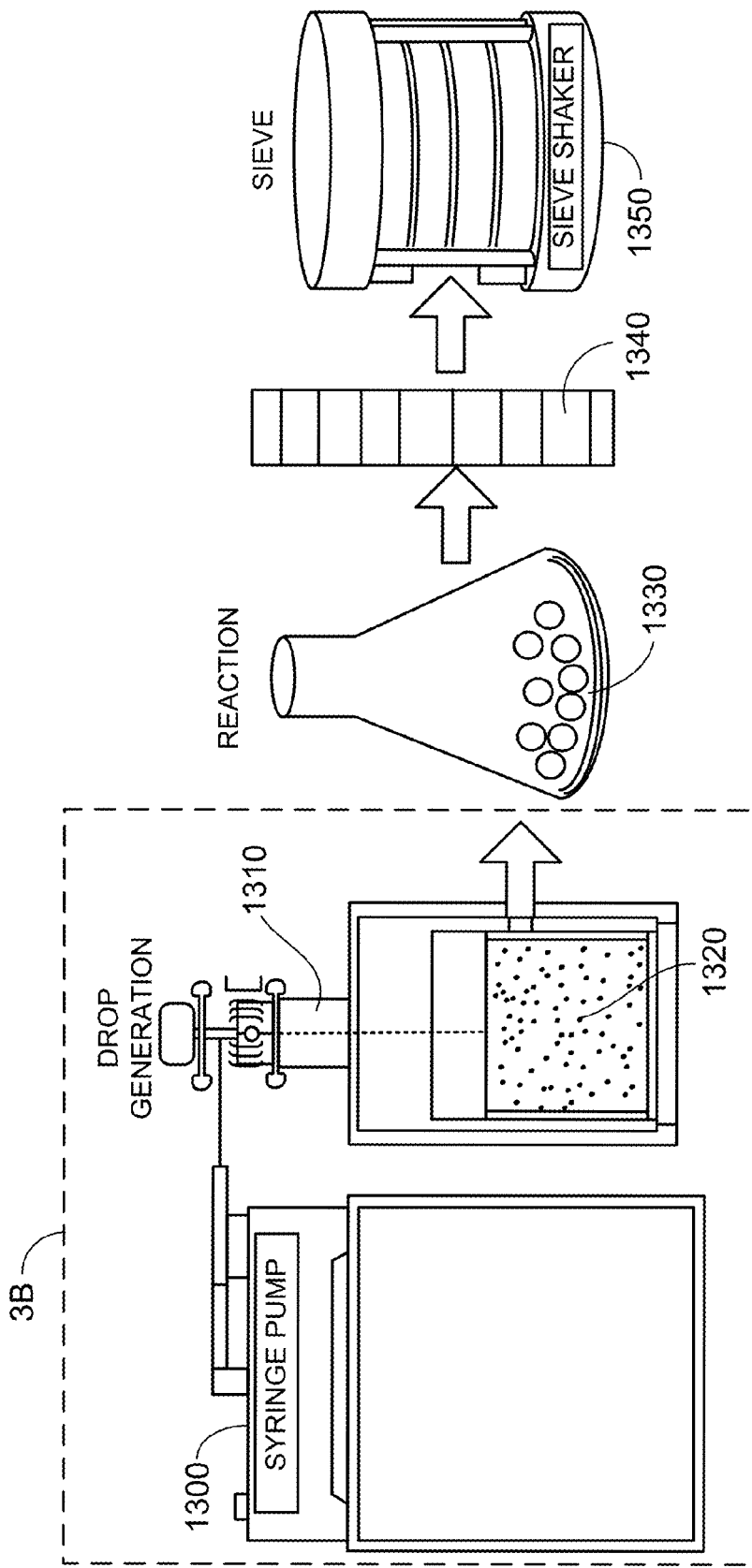
Figure 7B:
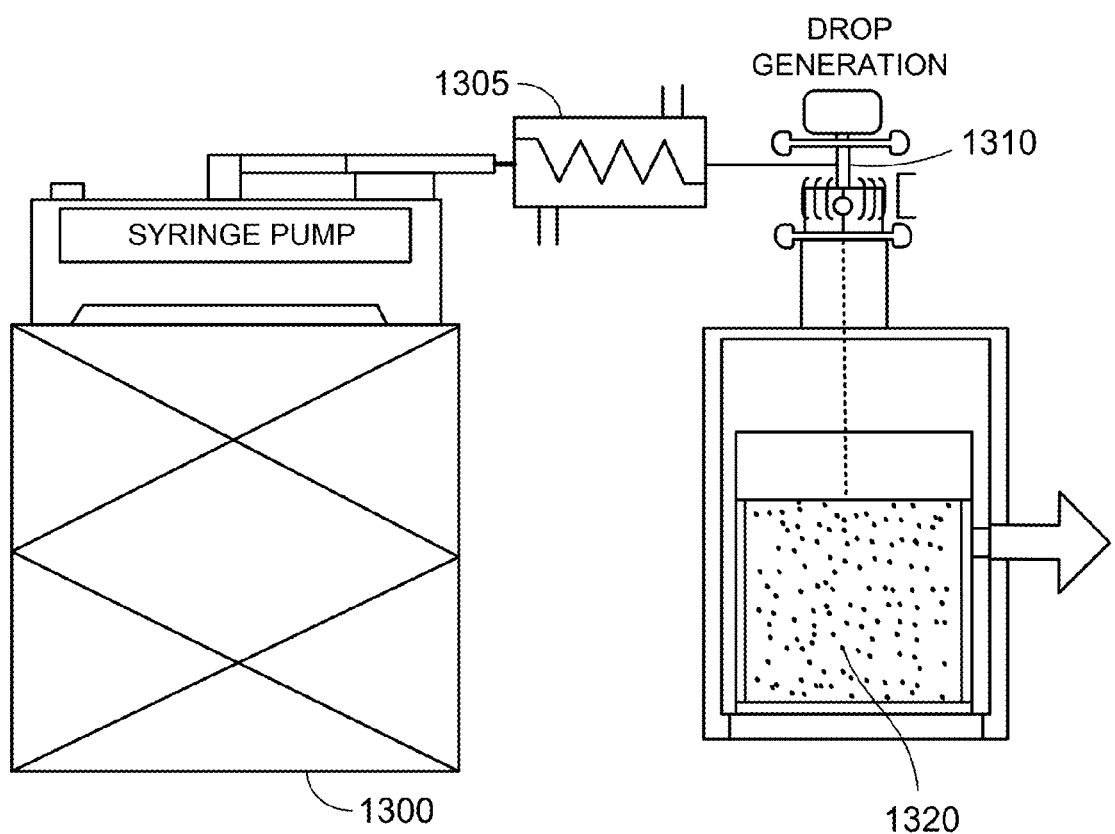
FIG. 7B is an enlarged schematic of region 3B in FIG. 7A.

FIG. 7A shows an embodiment of a system for producing embolic particles. The system includes a flow controller 1300, a drop generator 1310, a gelling vessel 1320, a reactor vessel 1330, a gel dissolution chamber 1340 and a filter 1350. As shown in FIG. 7B, flow controller 1300 delivers polymer solutions to a viscosity controller 1305, which heats the solution to reduce viscosity prior to delivery to drop generator 1310. The solution passes through an orifice in a nozzle in drop generator 1310, forming drops of the solution. The drops are then directed into gelling vessel 1320, where the drops are stabilized by gel formation. The gel-stabilized drops are transferred from gelling vessel 1320 to reactor vessel 1330, where the polymer in the gel-stabilized drops is reacted, forming precursor particles. The precursor particles are transferred to gel dissolution chamber 1340, where the gel is dissolved. The particles are then filtered in filter 1350 to remove debris, and are sterilized and packaged as an embolic composition including embolic particles.

In general, a base polymer and a gelling precursor are dissolved in water and mixed.

Examples of base polymers include polyvinyl alcohols, polyacrylic acids, polymethacrylic acids, poly vinyl sulfonates, carboxymethyl celluloses, hydroxyethyl celluloses, substituted celluloses, polyacrylamides, polyethylene glycols, polyamides, polyureas, polyurethanes, polyesters, polyethers, polystyrenes, polysaccharides, polylactic acids, polyethylenes, polymethylmethacrylates, polycaprolactones, polyglycolic acids, poly(lactic-co-glycolic) acids (e.g., poly(d-lactic-co-glycolic) acids) and copolymers or mixtures thereof. A preferred polymer is polyvinyl alcohol (PVA). The polyvinyl alcohol, in particular, is typically hydrolyzed in the range of from about 80 percent to about 99 percent. The weight average molecular weight of the base polymer can be, for example, in the range of from about 9000 to about 186,000 (e.g., from about 85,000 to about 146,000, from about 89,000 to about 98,000).

Gelling precursors include, for example, alginates, alginate salts, xanthan gums, natural gum, agar, agarose, chitosan, carrageenan, fucoidan, furcellaran, laminaran, hypnea, eucheuma, gum arabic, gum ghatti, gum karaya, gum tragacanth, hyaluronic acid, locust beam gum, arabinogalactan, pectin, amylopectin, other water soluble polysaccharides and other ionically cross-linkable polymers. A particular gelling precursor is sodium alginate. A preferred sodium alginate is high guluronic acid, stem-derived alginate (e.g., about 50 percent or more, about 60 percent or more guluronic acid) with a low viscosity (e.g., from about 20 centipoise to about 80 centipoise at 20° C.), which produces a high tensile, robust gel.

In some embodiments, the base polymer (e.g., PVA, such as high molecular weight PVA) can be dissolved in water by heating (e.g., above about 70° C. or more, about 121° C.), while the gelling precursor (e.g., an alginate) can be dissolved at room temperature. The base polymer (e.g., PVA) can be dissolved by mixing the base polymer and the gelling precursor (e.g., alginate) together in a vessel which is heated, e.g., to a temperature of at least about 50° C. (e.g., about 65° C. or more, about 75° C. or more, about 85° C. or more, about 95° C. or more, about 105° C. or more, about 115° C. or more, about 121° C.). In some embodiments, the mixture can be heated in an autoclave. Alternatively, the base polymer (e.g., PVA) can be disposed in water and heated. The gelling precursor (e.g., alginate) can subsequently be added at room temperature, to avoid exposing the alginate to high temperature. Heat can also be applied, for example, by microwave application.

In certain embodiments, such as when the base polymer is PVA and the gelling precursor is alginate, the mixture can be from about 6.5 weight percent to about 8.5 weight percent (e.g., about eight weight percent, about seven weight percent) base polymer and from about 1.5 weight percent to about 2.5 weight percent (e.g., about 1.75 weight percent, about two weight percent) gelling precursor.

In some embodiments, the base polymer/gelling precursor mixture can be introduced to a high pressure pumping apparatus, such as a syringe pump (e.g., model PHD4400, Harvard Apparatus, Holliston, Mass.), and then transferred to drop generator 1310. Alternatively or additionally, drop generator 1310 can contain a pressure control device that applies a pressure (e.g., from about 0.5 Bar to about 1.6 Bar) to the base polymer/gelling precursor mixture (a pressure head) to control the rate at which the mixture is transferred to drop generator 1310.

The pressure can be selected, for example, based on the size of the nozzle orifice and/or the desired viscosity of the base polymer/gelling precursor mixture, and/or the desired size of the particles. In general, for a given mixture, as the nozzle orifice is decreased, the pressure is increased. Generally, for a given mixture, as the desired viscosity of the mixture is decreased, the temperature is increased. As an example, in embodiments in which the nozzle orifice has a diameter of about 100 microns and the base polymer/gelling precursor mixture has a viscosity of from about 60 centipoise to about 100 centipoise, the pressure can be about 1.55 Bar. As another example, in embodiments in which the nozzle orifice has a diameter of about 200 microns and the base polymer/gelling precursor mixture has a viscosity of from about 60 centipoise to about 100 centipoise, the pressure can be about 0.55 Bar.

Referring to FIG. 7B, viscosity controller 1305 is a heat exchanger that circulates water at a predetermined temperature about the flow tubing between the pump and drop generator 1310. The base polymer/gelling precursor mixture flows into viscosity controller 1305, where the mixture is heated so that its viscosity is lowered to a desired level. Alternatively or additionally, the vessel containing the base polymer/gelling precursor mixture can be disposed in a heated fluid bath (e.g., a heated water bath) to heat the base polymer/gelling precursor mixture. In some embodiments (e.g., when the system does not contain viscosity controller 1305), flow controller 1300 and/or drop generator 1310 can be placed in a temperature-controlled chamber (e.g. an oven, a heat tape wrap) to heat the base polymer/gelling precursor mixture.

The temperature to which the base polymer/gelling precursor mixture is heated prior to transfer to drop generator 1310 can be selected, for example, based on the desired viscosity of the mixture and/or the size of the orifice in the nozzle. In general, for a given mixture, the lower the desired viscosity of the mixture, the higher the temperature to which the mixture is heated. Generally, for a given mixture, the smaller the diameter of the nozzle, the higher the temperature to which the mixture is heated. As an example, in embodiments in which nozzle has a diameter of from about 150 microns to about 1300 microns and the desired viscosity of the mixture is from about 90 centipoise to about 200 centipoise, the mixture can be heated to a temperature of from about 60° C. to about 70° C. (e.g., about 65° C.). As another example, in embodiments in which the nozzle has a diameter of from about 100 microns to about 200 centipoise, the mixture can be heated to a temperature of from about 70° C. to about 80° C. (e.g., about 75° C.).

Drop generator 1310 generates substantially spherical drops of a predetermined diameter by forcing a stream of the base polymer/gelling precursor mixture through the nozzle orifice. The nozzle is subjected to a periodic disturbance to break up the jet stream of the mixture into drops of the mixture. The jet stream can be broken into drops by vibratory action generated, for example, by an electrostatic or piezoelectric element. The drop size can be controlled, for example, by controlling the nozzle orifice diameter, base polymer/gelling precursor flow rate, nozzle vibration amplitude, and nozzle vibration frequency. In general, holding other parameters constant, increasing the nozzle orifice diameter results in formation of larger drops, and increasing the flow rate results in larger drops. Generally, holding other parameters constant, increasing the nozzle vibration amplitude results in larger drops, and reducing the nozzle vibration frequency results in larger drops. In general, the nozzle orifice diameter can be about 500 microns or less (e.g., about 400 microns or less, about 300 microns or less, about 200 microns or less, about 100 microns or less) and/or about 50 microns or more. The flow rate through the drop generator is typically from about one milliliter per minute to about 12 milliliters per minute. Generally, the nozzle frequency used can be about 0.1 KHz or more (e.g., about 0.8 KHz or more, about 1.5 KHz or more, about 1.75 KHz or more, about 1.85 KHz or more, about 2.5 KHz or more, from about 0.1 KHz to about 0.8 KHz). In general, the nozzle vibration amplitude is larger than the width of the jet stream. The drop generator can have a variable nozzle vibration amplitude setting, such that an operator can adjust the amplitude of the nozzle vibration. In some embodiments, the nozzle vibration amplitude is set at between about 80 percent and about 100 percent of the maximum setting.

In some embodiments, drop generator 1310 can charge the drops after formation, such that mutual repulsion between drops prevents drop aggregation as the drops travel from drop generator 1310 to gelling vessel 1320. Charging may be achieved, for example, by an electrostatic charging device such as a charged ring positioned downstream of the nozzle.

An example of a commercially available electrostatic drop generator is the model NISCO Encapsulation unit VAR D (NISCO Engineering, Zurich, Switzerland). Another example of a commercially available drop generator is the Inotech Encapsulator unit IE-50R/NS (Inotech AG, Dottikon, Switzerland).

Drops of the base polymer and gelling precursor mixture are captured in gelling vessel 1320. The distance between gelling vessel 1320 and the orifice of the nozzle in drop generator 1310 is generally selected so that the jet stream of the base polymer/gelling precursor mixture is substantially broken up into discrete drops before reaching gelling vessel 1320. In some embodiments, the distance from the nozzle orifice to the mixture contained in gelling vessel 1320 is from about five inches to about six inches.

The mixture contained in gelling vessel 1320 includes a gelling agent which interacts with the gelling precursor to stabilize drops by forming a stable gel. Suitable gelling agents include, for example, a divalent cation such as alkali metal salt, alkaline earth metal salt or a transition metal salt that can ionically cross-link with the gelling agent. An inorganic salt, for example, a calcium, barium, zinc or magnesium salt can be used as a gelling agent. In embodiments, particularly those using an alginate gelling precursor, a suitable gelling agent is calcium chloride. The calcium cations have an affinity for carboxylic groups in the gelling precursor. The cations complex with carboxylic groups in the gelling precursor, resulting in encapsulation of the base polymer in a matrix of gelling precursor.

Without wishing to be bound by theory, it is believed that in some embodiments (e.g., when forming particles having a diameter of about 500 microns or less), it can be desirable to reduce the surface tension of the mixture contained in gelling vessel 1320. This can be achieved, for example, by heating the mixture in gelling vessel 1320 (e.g., to a temperature greater than room temperature, such as a temperature of about 30° C. or more), by bubbling a gas (e.g., air, nitrogen, argon, krypton, helium, neon) through the mixture contained in gelling vessel 1320, by stirring (e.g., via a magnetic stirrer) the mixture contained in gelling vessel 1320, by including a surfactant in the mixture containing the gelling agent, and/or by forming a mist containing the gelling agent above the mixture contained in gelling vessel 1320 (e.g., to reduce the formation of tails and/or enhance the sphericity of the particles).

Figure 8:
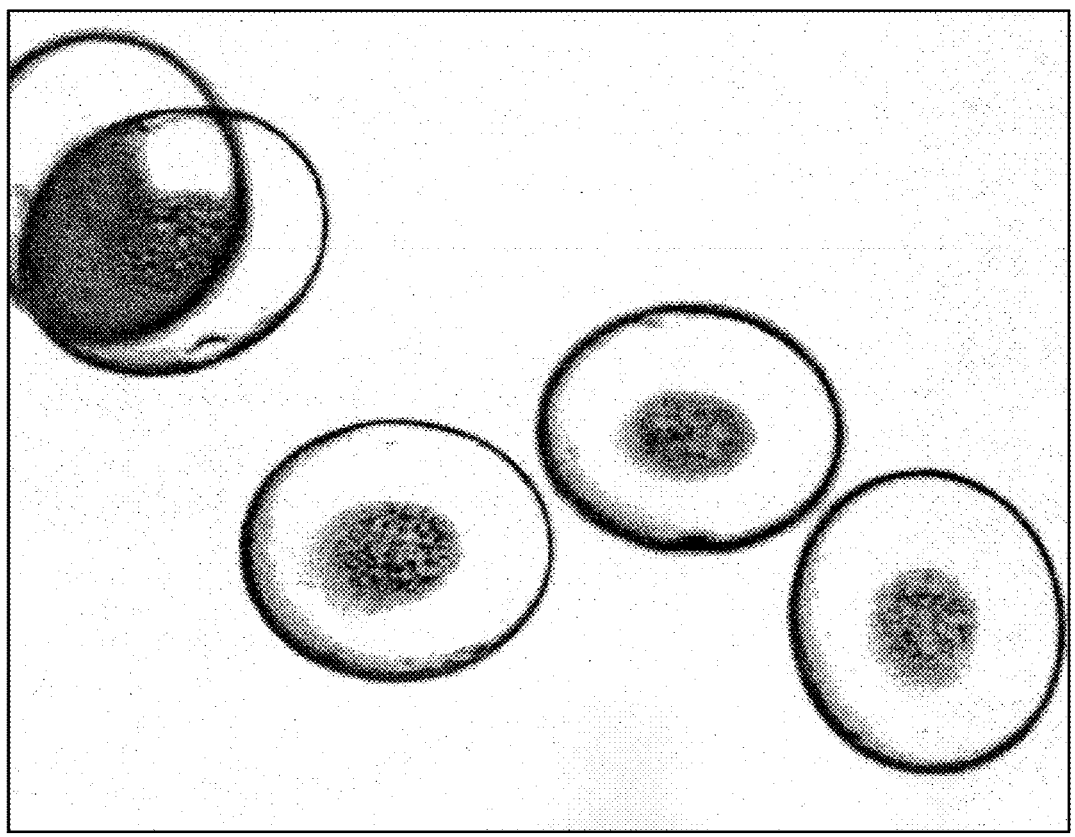
FIG. 8 is a photograph of gel-stabilized drops.

FIG. 8 shows a photo-image of the gelled particles. As evident, a pore structure in the particle forms in the gelling stage. The concentration of the gelling agent can affect pore formation in the particle, thereby controlling the porosity gradient in the particle. Adding non-gelling ions (e.g., sodium ions) to the gelling solution can reduce the porosity gradient, resulting in a more uniform intermediate porosity throughout the particle. In embodiments, the gelling agent is, for example, from about 0.01 weight percent to about 10 weight percent (e.g., from about one weight percent to about five weight percent, about two weight percent) in deionized water. In embodiments, particles, including gelling agent and a pore structure, can be used in embolic compositions.

Following drop stabilization, the gelling solution can be decanted from the solid drops, or the solid drops can be removed from the gelling solution by sieving. The solid drops are then transferred to reactor vessel 1330, where the base polymer in the solid drops is reacted (e.g., cross-linked) to produce precursor particles.

Reactor vessel 1330 contains an agent that chemically reacts with the base polymer to cause cross-linking between polymer chains and/or within a polymer chain. The agent diffuses into the solid drops from the surface of the particle in a gradient which, it is believed, provides more cross-linking near the surface of the solid drop than in the body and center of the drop. Reaction is greatest at the surface of a solid drop, providing a stiff, abrasion-resistant exterior. For polyvinyl alcohol, for example, vessel 1330 includes one or more aldehydes, such as formaldehyde, glyoxal, benzaldehyde, aterephthalaldehyde, succinaldehyde and glutaraldehyde for the acetalization of polyvinyl alcohol. Vessel 1330 also includes an acid, for example, strong acids such as sulfuric acid, hydrochloric acid, nitric acid and weak acids such as acetic acid, formic acid and phosphoric acid. In embodiments, the reaction is primarily a 1,3-acetalization: 1

This intra-chain acetalization reaction can be carried out with relatively low probability of inter-chain cross-linking, as described in John G. Pritchard, "Poly(Vinyl Alcohol) Basic Properties and Uses (Polymer Monograph, vol. 4) (see p. 93-97), Gordon and Breach, Science Publishers Ltd., London, 1970, which is incorporated herein by reference. Because the reaction proceeds in a random fashion, some OH groups along a polymer chain might not react with adjacent groups and may remain unconverted.

Adjusting for the amounts of aldehyde and acid used, reaction time and reaction temperature can control the degree of acetalization. In embodiments, the reaction time is from about five minutes to about one hour (e.g., from about 10 minutes to about 40 minutes, about 20 minutes). The reaction temperature can be, for example, from about 25° C. to about 150° C. (e.g., from about 75° C. to about 130° C., about 65° C.). Reactor vessel 1330 can be placed in a water bath fitted with an orbital motion mixer. The cross-linked precursor particles are washed several times with deionized water to neutralize the particles and remove any residual acidic solution.

The precursor particles are transferred to dissolution chamber 1340, where the gelling precursor is removed (e.g., by an ion exchange reaction). In embodiments, sodium alginate is removed by ion exchange with a solution of sodium hexa-metaphosphate (EM Science). The solution can include, for example, ethylenediaminetetracetic acid (EDTA), citric acid, other acids, and phosphates. The concentration of the sodium hexa-metaphosphate can be, for example, from about one weight percent to about 20 weight percent (e.g., from about one weight percent to about ten weight percent, about five weight percent) in deionized water. Residual gelling precursor (e.g., sodium alginate) can be measured by assay (e.g., for the detection of uronic acids in, for example, alginates containing mannuronic and guluronic acid residues). A suitable assay includes rinsing the particles with sodium tetraborate in sulfuric acid solution to extract alginate, combining the extract with metahydroxydiphenyl colormetric reagent, and determining concentration by UV/VIS spectroscopy. Testing can be carried out by alginate suppliers such as FMC Biopolymer, Oslo, Norway. Residual alginate may be present in the range of, for example, from about 20 weight percent to about 35 weight percent prior to rinsing, and in the range of from about 0.01 weight percent to about 0.5 weight percent (e.g., from about 0.1 weight percent to about 0.3 weight percent, about 0.18 weight percent) in the particles after rinsing for 30 minutes in water at about 23° C.

The particles are filtered through filter 1350 to remove residual debris. Particles of from about 100 microns to about 300 microns can filtered through a sieve of about 710 microns and then a sieve of about 300 microns. The particles can then be collected on a sieve of about 20 microns. Particles of from about 300 to about 500 microns can filtered through a sieve of about 710 microns and then a sieve of about 500 microns. The particles can then be collected on a sieve of about 100 microns. Particles of from about 500 to about 700 microns can be filtered through a sieve of about 1000 microns, then filtered through a sieve of about 710 microns, and then a sieve of about 300 microns. The particles can then be collected in a catch pan. Particles of from about 700 to about 900 microns can be filtered through a sieve of 1000 microns and then a sieve of 500 microns. The particles can then be collected in a catch pan. Particles of from about 900 to about 1200 microns can filtered through a sieve of 1180 microns and then a sieve of 710 microns. The particles can then be collected in a catch pan.

The particles are then packaged. Typically, from about one milliliter to about five milliliters of particles are packaged in from about five milliliters to about ten milliliters of saline. The filtered particles then are typically sterilized by a low temperature technique, such as e-beam irradiation. In embodiments, electron beam irradiation can be used to pharmaceutically sterilize the particles (e.g., to reduce bioburden). In e-beam sterilization, an electron beam is accelerated using magnetic and electric fields, and focused into a beam of energy. The resultant energy beam can be scanned by means of an electromagnet to produce a "curtain" of accelerated electrons. The accelerated electron beam penetrates the collection of particles, destroying bacteria and mold to sterilize and reduce the bioburden in the particles. Electron beam sterilization can be carried out by sterilization vendors such as Titan Scan, Lima, Ohio.

The embolic compositions can be used in the treatment of, for example, fibroids, tumors, internal bleeding, AVMs, hypervascular tumors, fillers for aneurysm sacs, endoleak sealants, arterial sealants, puncture sealants and occlusion of other lumens such as fallopian tubes. Fibroids can include uterine fibroids which grow within the uterine wall (intramural type), on the outside of the uterus (subserosal type), inside the uterine cavity (submucosal type), between the layers of broad ligament supporting the uterus (interligamentous type), attached to another organ (parasitic type), or on a mushroom-like stalk (pedunculated type). Internal bleeding includes gastrointestinal, urinary, renal and varicose bleeding. AVMs are for example, abnormal collections of blood vessels, e.g. in the brain, which shunt blood from a high pressure artery to a low pressure vein, resulting in hypoxia and malnutrition of those regions from which the blood is diverted.

The magnitude of a dose of an embolic composition can vary based on the nature, location and severity of the condition to be treated, as well as the route of administration. A physician treating the condition, disease or disorder can determine an effective amount of embolic composition. An effective amount of embolic composition refers to the amount sufficient to result in amelioration of symptoms or a prolongation of survival of the patient. The embolic compositions can be administered as pharmaceutically acceptable compositions to a patient in any therapeutically acceptable dosage, including those administered to a patient intravenously, subcutaneously, percutaneously, intratracheally, intramuscularly, intramucosaly, intracutaneously, intraarticularly, orally or parenterally.

In some embodiments, a composition containing the particles can be used to prophylactically treat a condition.

Compositions containing the particles can be prepared in calibrated concentrations of the particles for ease of delivery by the physician. Suspensions of the particles in saline solution can be prepared to remain stable (e.g., to not precipitate) over a duration of time. A suspension of the particles can be stable, for example, for from about one minute to about 20 minutes (e.g. from about one minute to about ten minutes, from about two minutes to about seven minutes, from about three minutes to about six minutes). The concentration of particles can be determined by adjusting the weight ratio of the particles to the physiological solution. If the weight ratio of the particles is too small, then too much liquid could be injected into a blood vessel, possibly allowing the particles to stray into lateral vessels. In some embodiments, the physiological solution can contain from about 0.01 weight percent to about 15 weight percent of the particles. A composition can include a mixture of particles, such as particles having the pore profiles discussed above, particles with other pore profiles, and/or non-porous particles.

While certain embodiments have been described, the invention is not so limited.

As an example, particles can be used for embolic applications without removal of the gelling agent (e.g. alginate). Such particles can be prepared, for example, as described above, but without removing the alginate from the particle after cross-linking.

As another example, while substantially spherical particles are preferred, non-spherical particles can be manufactured and formed by controlling, for example, drop formation conditions. In some embodiments, nonspherical particles can be formed by post-processing the particles (e.g., by cutting or dicing into other shapes).

Moreover, in some embodiments the particles can include one or more therapeutic agents (e.g., drugs). The therapeutic agent(s) can be in and/or on the particles. Therapeutic agents include agents that are negatively charged, positively charged, amphoteric, or neutral. Therapeutic agents can be, for example, materials that are biologically active to treat physiological conditions; pharmaceutically active compounds; gene therapies; nucleic acids with and without carrier vectors; oligonucleotides; gene/vector systems; DNA chimeras; compacting agents (e.g., DNA compacting agents); viruses; polymers; hyaluronic acid; proteins (e.g., enzymes such as ribozymes); cells (of human origin, from an animal source, or genetically engineered); stem cells; immunologic species; nonsteroidal anti-inflammatory medications; oral contraceptives; progestins; gonadotrophin-releasing hormone agonists; chemotherapeutic agents; and radioactive species (e.g., radioisotopes, radioactive molecules). Non-limiting examples of therapeutic agents include anti-thrombogenic agents; antioxidants; angiogenic and anti-angiogenic agents and factors; anti-proliferative agents (e.g., agents capable of blocking smooth muscle cell proliferation); anti-inflammatory agents; calcium entry blockers; antineoplastic/antiproliferative/anti-mitotic agents (e.g., paclitaxel, doxorubicin, cisplatin); antimicrobials; anesthetic agents; anti-coagulants; vascular cell growth promoters; vascular cell growth inhibitors; cholesterol-lowering agents; vasodilating agents; agents which interfere with endogenous vasoactive mechanisms; and survival genes which protect against cell death. Therapeutic agents are described in co-pending U.S. patent application Ser. No. 10/615,276, filed on Jul. 8, 2003, and entitled "Agent Delivery Particle", which is incorporated herein by reference.

In addition, in some embodiments (e.g., where the base polymer is a polyvinyl alcohol and the gelling precursor is alginate), after contacting the particles with the gelling agent but before cross-linking, the particles can be physically deformed into a specific shape and/or size. For example, the particles can be molded, compressed, punched, and/or agglomerated with other particles. After shaping, the base polymer (e.g., polyvinyl alcohol) can be cross-linked, optionally followed by substantial removal of the gelling precursor (e.g., alginate). Particle shaping is described, for example, in co-pending U.S. patent application Ser. No. 10/402,068, filed Mar. 28, 2003, and entitled "Forming a Chemically Cross-Linked Particle of a Desired Shape and Diameter", which is incorporated herein by reference.

In certain embodiments, the gelling precursor of coating material 130 is a sodium alginate solution having a sodium alginate concentration of about ten percent or less (e.g., about one percent to about ten percent). In some embodiments, the gelling precursor is a high guluronic acid, stem-derived alginate (e.g., about 50 percent or more, about 60 percent or more guluronic acid) with a low viscosity (e.g., from about 20 centipoise to about 80 centipoise at 20° C.), which produces a high tensile, robust gel. While the gelling precursor has been described as being sodium alginate, the gelling precursor can be any of various materials or compositions capable of being formed into a coating (e.g., a gel coating). In some embodiments, the gelling precursor is formed of a biocompatible material. Examples of suitable materials with which to form the gelling precursor include alginates, alginate salts, xanthan gums, natural gum, agar, agarose, chitosan, carrageenan, fucoidan, furcellaran, laminaran, hypnea, eucheuma, gum arabic, gum ghatti, gum karaya, gum tragacanth, hyalauronic acid, locust beam gum, arabinogalactan, pectin, amylopectin, other water soluble polysaccharides and other ionically cross-linkable polymers.

In some embodiments, particularly those using an alginate gelling precursor, gelling agent 135 can be calcium chloride. The calcium cations have an affinity for carboxylic groups in the gelling precursor. The cations complex with carboxylic groups in the gelling precursor, resulting in encapsulation of the polymer by the gelling precursor. While gelling agent 135 has been described as being calcium chloride, gelling agent 135 can be any material capable of reacting with the gelling precursor of coating material 130 to form coatings (e.g., gel coatings) around particles 105. Examples of such materials include a charged polymer (e.g., polyacrylic acid), or a divalent cation such as alkali metal salt, alkaline earth metal salt or a transition metal salt that can ionically cross-link with the gelling precursor. An inorganic salt, for example, a calcium, barium, zinc or magnesium salt can be used as a gelling agent.

As noted above, FIG. 2 shows coated particle 200, which can be formed using the process described above. The therapeutic agent of coating material 130 (shown in FIG. 1) is included in (e.g., is encapsulated by) gel coating 230. In some embodiments, coated particle 200 has a diameter of about 3,500 microns or less (e.g., about 300 microns or less; about 2,500 microns or less; about 2,000 microns or less; about 1,500 microns or less; about 1,200 microns or less; about 900 microns or less; about 700 microns or less; about 500 microns or less; about 400 microns or less; about 300 microns or less; about 100 microns or less) and/or about ten microns or more (e.g., about 100 microns or more; about 300 microns or more; about 400 microns or more; about 500 microns or more; about 700 microns or more; about 900 microns or more; about 1,200 microns or more; about 1,500 microns or more; about 2,000 microns or more; about 2,500 microns or more; about 3,000 microns or more).

A plurality of coated particles 200 (e.g., formed by the process described above) can be passed through a sieve or a series of sieves to remove residual debris form the coated particles. After being passed through the sieve(s), coated particles 200 can be packaged. Typically, about one milliliter to about five milliliters of coated particles are packaged in about five milliliters to about ten milliliters of a carrier fluid (e.g., a pharmaceutically acceptable carrier, such as a saline solution, a contrast agent, or both) to form an embolic composition. In general, the density of the coated particles (e.g., as measured in grams of material per unit volume) is such that they can be readily suspended in the carrier fluid. In some embodiments, the density of a coated particle is from about 1.1 grams per cubic centimeter to about 1.4 grams per cubic centimeter. As an example, for suspension in a saline-contrast solution, the density can be from about 1.2 grams per cubic centimeter to about 1.3 grams per cubic centimeter.

Following packaging, the composition of coated particles 200 and the carrier fluid can be sterilized using a low temperature sterilizing technique, such as electron beam irradiation. In electron beam sterilization, an electron beam is accelerated using magnetic and electric fields, and focused into a beam of energy. The resultant energy beam can be scanned by means of an electromagnet to produce a "curtain" of accelerated electrons. The accelerated electron beam penetrates the collection of coated particles, destroying bacteria and mold to sterilize and reduce the bioburden in the coated particles. Electron beam sterilization can be carried out by sterilization vendors such as Titan Scan, Lima, Ohio.

Figure 3B:
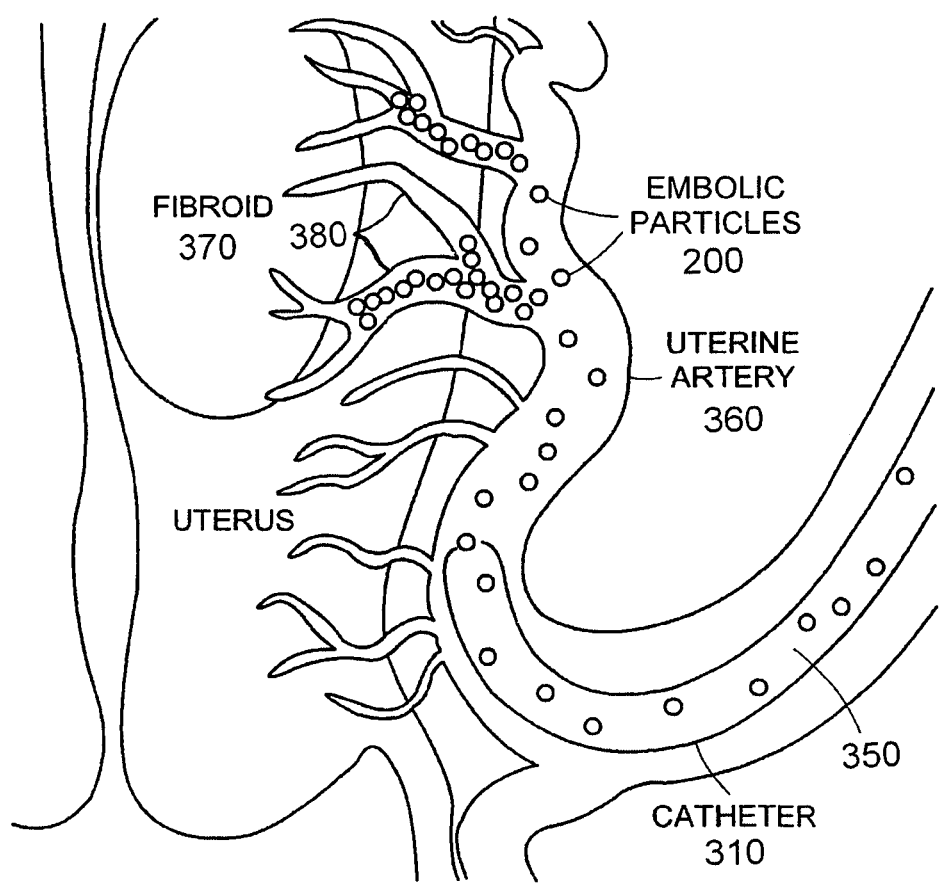
FIG. 3B is an enlarged view of region 3B in FIG. 3A.

FIGS. 3A and 3B show an embolization procedure in which the embolic composition (e.g., coated particles 200 and the carrier fluid) is injected into a vessel through an instrument, such as a catheter 310. Catheter 310 is connected to a syringe barrel 320 with a plunger 330. The embolic composition is loaded into syringe barrel 320, and catheter 310 is inserted, for example, into a femoral artery 340 of a patient. Plunger 330 of syringe barrel 320 is then compressed to deliver the embolic composition through catheter 310 into a lumen 350 of a uterine artery 360 that leads to a fibroid 370 located in the uterus of the patient. The embolic composition can, for example, occlude uterine artery 360.

As shown in FIG. 3B, uterine artery 360 is subdivided into smaller uterine vessels 380 (e.g., having a diameter of about two millimeters or less) which feed fibroid 370. Coated particles 200 in the embolic composition partially or totally fill the lumen of uterine artery 360, either partially or completely occluding the lumen of the uterine artery 360 that feeds uterine fibroid 370. In some embodiments, as the gel coating degrades, the therapeutic agent is released from particles 200 and delivered within the vessel of the patient. The therapeutic agent can, for example, help to alleviate pain resulting from the above-described procedure.

As an alternative to or in addition to treating uterine fibroids, the above-described embolic compositions (e.g., coated particles 200 and carrier fluid) can be used to treat any of various other medical conditions. The compositions, for example, can be used in the treatment of tumors, internal bleeding, arteriovenous malformations (AVMs), and/or hypervascular tumors. The compositions can be used as fillers for aneurysm sacs, AAA sac (Type II endoleaks), endoleak sealants, arterial sealants, and/or puncture sealants, and/or can be used to provide occlusion of other lumens such as fallopian tubes. Internal bleeding includes gastrointestinal, urinary, renal and varicose bleeding. AVMs are, for example, abnormal collections of blood vessels, e.g., in the brain, which shunt blood from a high pressure artery to a low pressure vein, resulting in hypoxia and malnutrition of those regions from which the blood is diverted. In some embodiments, a composition containing the particles can be used to prophylactically treat a condition.

Furthermore, coated particles 200 or a composition including coated particles 200 can be used for tissue bulking. Coated particles 200, for example, can be placed (e.g., injected) into tissue adjacent a body passageway. Coated particles 200 can narrow the passageway, thereby providing bulk and allowing the tissue to constrict the passageway more easily. Coated particles 200 can be placed in the tissue according to a number of different methods, for example, percutaneously, laparoscopically, and/or through a catheter. In certain embodiments, a cavity can be formed in the tissue, and coated particles 200 can be placed in the cavity. Particle tissue bulking can be used to treat, for example, intrinsic sphincteric deficiency (ISD), vesicoureteral reflux, gastroesophageal reflux disease (GERD), and/or vocal cord paralysis (e.g., to restore glottic competence in cases of paralytic dysphonia). In some embodiments, particle tissue bulking can be used to treat urinary incontinence and/or fecal incontinence. Coated particles 200 can be used as a graft material or a filler to fill and/or to smooth out soft tissue defects, such as for reconstructive or cosmetic applications (e.g., surgery). Examples of soft tissue defect applications include cleft lips, scars (e.g., depressed scars from chicken pox or acne scars), indentations resulting from liposuction, wrinkles (e.g., glabella frown wrinkles), and soft tissue augmentation of thin lips. Tissue bulking is described, for example, in co-pending U.S. Patent Application Publication No. US 2003/0233150 A1, published on Dec. 18, 2003, which is incorporated herein by reference.

While certain embodiments have been described, other embodiments are possible.

Figure 4:
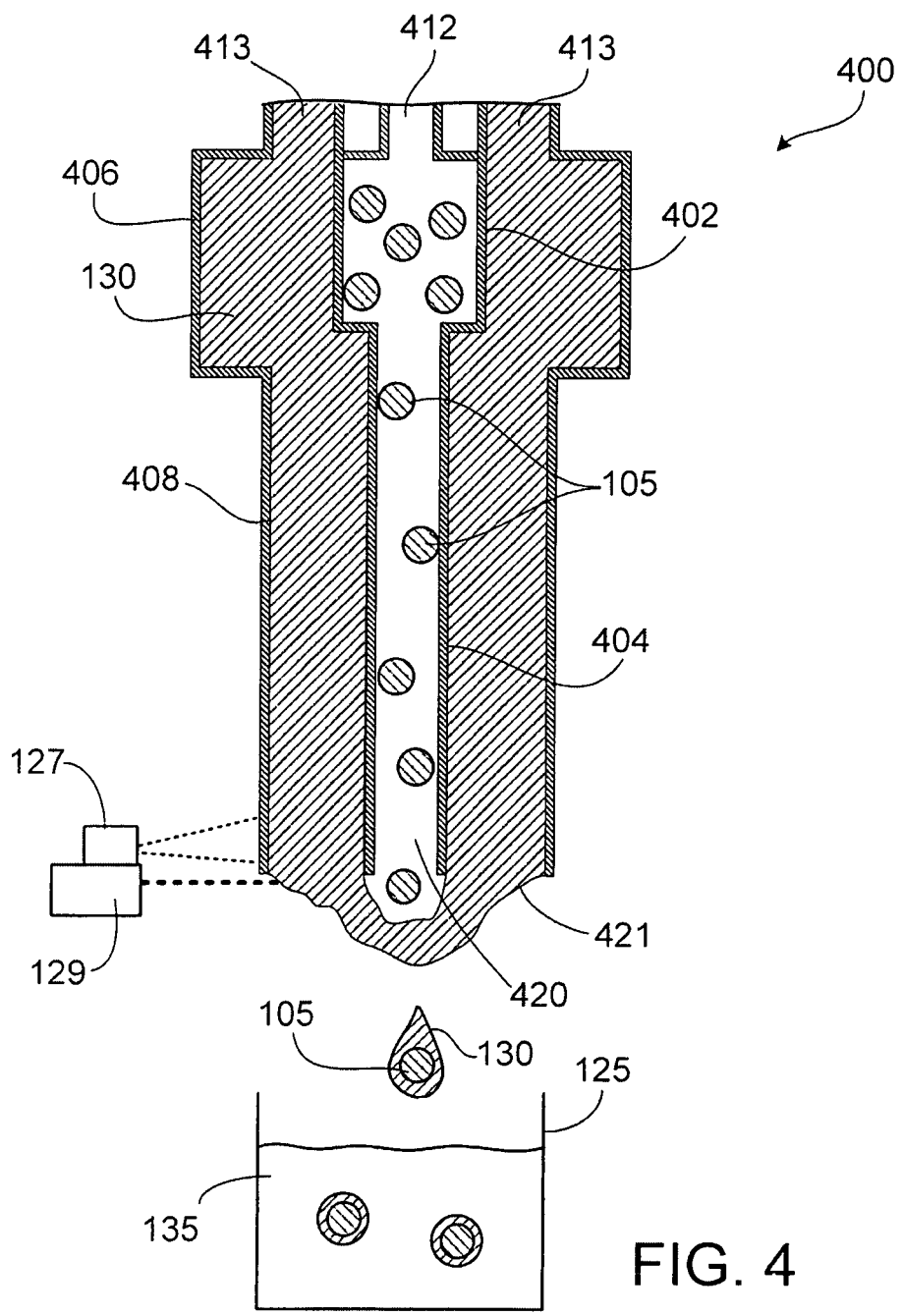
FIG. 4 is a cross-sectional view of an embodiment of a particle-coating system.

As an example, while tube 115 includes a single lumen, in some embodiments, the tube through which the stream of particles 105 and gelling agent 130 flow is a concentric tube. As shown in FIG. 4, for example, system 400 includes a particle pumping chamber 402 fluidly connected to an inner tube 404. System 400 also includes a coating material pumping chamber 406 fluidly connected to an outer tube 408. Inner tube 404 is positioned coaxially within outer tube 408.

During use, particles 105 are introduced into pumping chamber 402 via inlet 412, and coating material 130 is introduced into pumping chamber 406 via inlet 413. Particles 105 are pumped through inner tube 104, and coating material 130 is pumped through outer tube 408. In certain embodiments, inner tube 406 has a diameter that is only slightly larger than particles 105, which can allow the stream of particles to pass through inner tube 404 in a single file fashion. In some embodiments, particles 105 and coating material 130 flow through their respective tubes at substantially the same rate. As particles 105 and coating material 130 reach outlets 420 and 421, respectively, the two streams merge and particles 105 become surrounded or partially surrounded by coating material 130 to form a composition of particles 105 and coating material 130. Droplets of the composition are then formed by separating device 129 and introduced to gelling agent 135 to form coated particles 200 (shown in FIG. 2).

Figure 5:
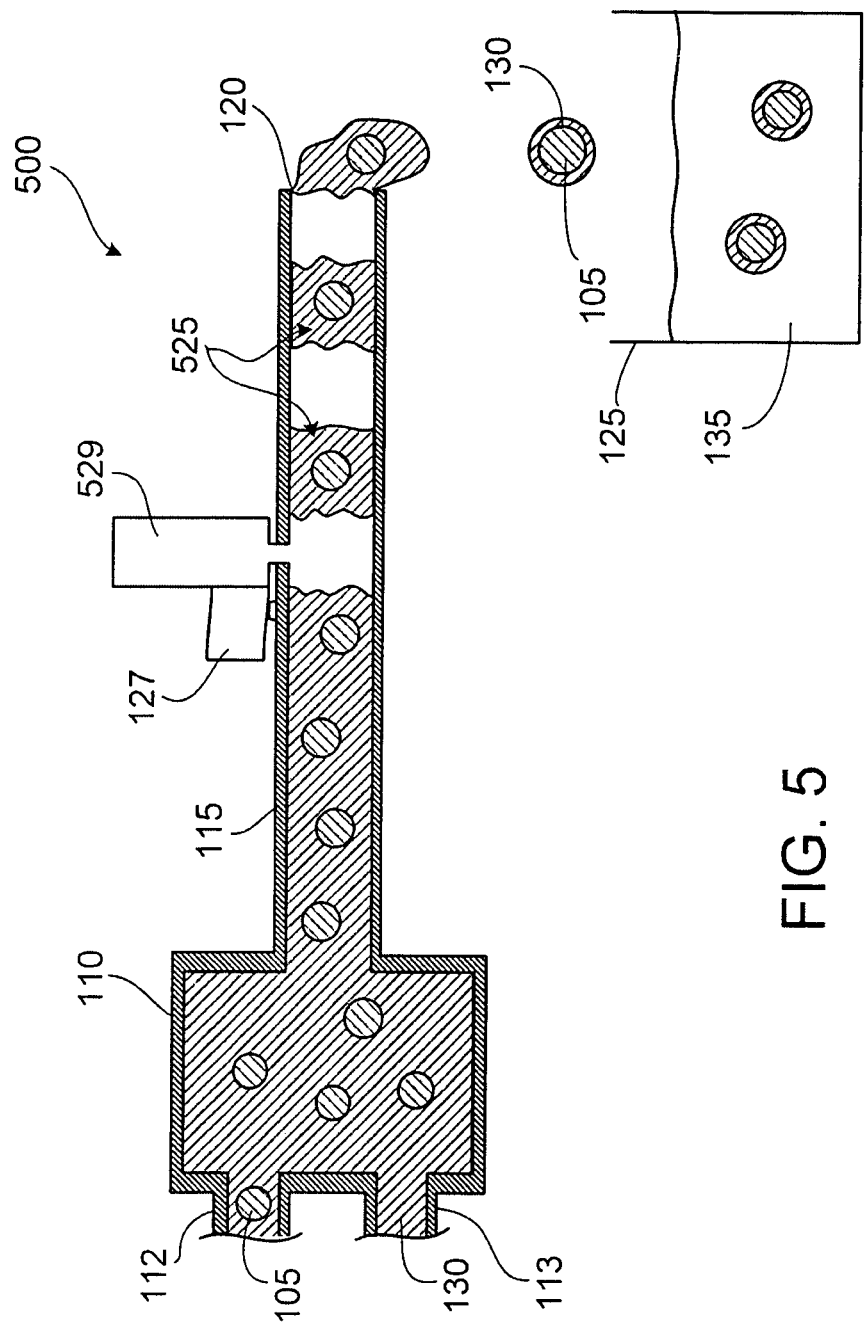
FIG. 5 is a cross-sectional view of an embodiment of a particle-coating system.

As an additional example, in certain embodiments, the stream of the composition of particles 105 and coating material 130 is broken up within the tube to form one or more discrete portions of the composition. Referring to FIG. 5, for example, a system 500 includes a gas injection device 529 (e.g., an air injection device) in communication with sensing device 127. Gas injection device 529 can, for example, include a solenoid valve attached to an outlet of a pressurized air tank. As the composition of particles 105 and coating material 130 pass through tube 115, gas injection device 529 (e.g., the solenoid valve of gas injection device 529) is activated to force gas (e.g., air) into the stream of the composition. In some embodiments, gas injection device 529 includes a one-way valve arranged near its opening to help prevent coating material 130 from entering gas injection device 529. As a result of the gas being forced into the stream, a pocket of gas is created within the stream, thereby separating one or more discrete portions 525 of the composition from the remainder of the composition and creating a discontinuous stream. Gas injection device 529 can communicate with sensing device 127 in order to help ensure that the air is injected between adjacent particles so that discrete portions 525 include one particle 105 surrounded by coating material 130. Upon reaching outlet 120 of tube 115, discrete portions 525 of the composition become droplets, which are combined with gelling agent 135 to form coated particles.

Figure 6:
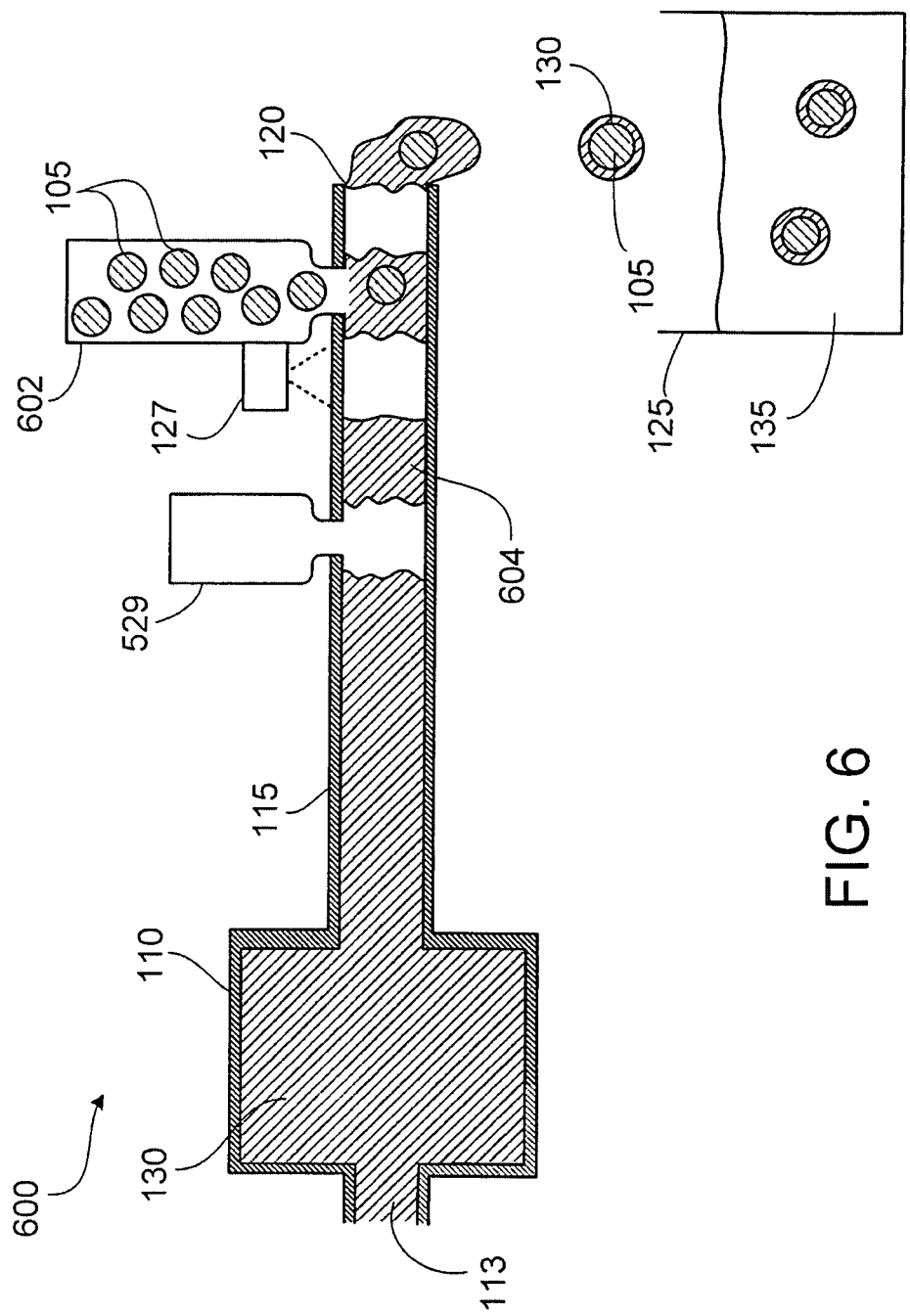
FIG. 6 is a cross-sectional view of an embodiment of a particle-coating system.

As a further example, in some embodiments, particles 105 are introduced into discrete portions of coating material 130 formed within tube 115. Referring to FIG. 6, for example, a system 600 includes a particle injection device 602 located downstream from gas injection device 529. Typically, both devices 529 and 602 are in communication with sensing device 127. During use, coating material 130 is introduced to pump 110 and forced through tube 115. Gas injection device 529 injects air into the stream of coating material 130 to break the stream into multiple discrete portions 604, thereby forming a discontinuous stream of coating material 130. As discrete portions 604 pass by particle injection device 602, particle injection device 602 is activated to inject particles 105 into discrete portions 604. In order to help ensure that particle injection device 602 is activated at the appropriate time (e.g., when one of the discrete portions 604 is adjacent the outlet of particle injection device 602), sensing device 127 can be arranged to detect the location of discrete portions 604 as they pass through tube 115, and this information can be communicated to particle injection device 127. System 600 can be operated such that one particle 105 is introduced into each discrete portion 604. The discrete portions 604, including particles 105, can then be introduced to gelling agent 135 to form coated particle 200 (shown in FIG. 2).

As an alternative to or in addition to injecting gas (e.g., air) into the stream to form create discontinuity within the stream (e.g., to form multiple discrete portions within the tube), any of various other types of energy can be injected into the stream. In some embodiments, for example, laser energy is injected into the stream to create discontinuity within the stream in the tube. In certain embodiments, the laser energy interacts with the material flowing through the tube to create a gas pocket.

As an additional example, while the activation of separating device 129 and injection devices 529, 602 is described above as being controlled by communication between sensing device 127 and the separating and activation devices, other control techniques can be used. In some embodiments, for example, separating device 129 and/or injection devices 529, 602 are controlled as a function of the flow rate of the material passing through the tube. For example, separating device 129 and/or injection devices 529, 602 can be periodically activated to repeatedly introduce energy (e.g., laser energy and/or gas) into the stream at a location between adjacent particles.

As another example, in some embodiments, the system can be arranged such that the force of gravity, rather than the force created by a pump or other flow control mechanism, causes the composition of the particles and the mixture to flow through the tube. The tube, for example, can be arranged in a substantially vertical position. In certain embodiments, mixture can be selected to have a viscosity that permits the composition to flow through the tube at a desired flow rate. The diameter of the tube can alternatively or additionally be selected so as to provide a desired flow rate of the composition through the tube.

As another example, in some embodiments particles 105 are porous and/or include one or more cavities. In certain embodiments, particles 105 have a substantially uniform pore structure. In some embodiments, particles 105 have a non-uniform pore structure. For example, particles 105 can have a substantially non-porous interior region and a porous exterior region. Examples of porous particles are described in U.S. Published Patent Application No. US 2004/0096662 A1, published on May 20, 2004, which is incorporated by reference herein.

As a further example, while particles 105 are shown above as being substantially round, particles 105 can alternatively or additionally be any of various other shapes. Particles 105, for example, can be oval-shaped, rectangular, triangular, and/or cylindrical.

As an additional example, while coating 230 of coating particles 200 has been described as including the therapeutic agent, in some embodiments, coating 230 includes no therapeutic agent. Coating 230 of coated particles 200 can, for example, include only a gel material. Methods and systems similar to those described in the embodiments above can be used to form such coated particles. However, coating material 130 of those systems can include only the gelling precursor.

As a further example, in some embodiments coating 230 includes only the therapeutic agent. Systems and methods similar to those described in the embodiments above can be used to form such coated particles. However, coating material 130 of those systems can include only the therapeutic agent.

As an additional example, in some embodiments, coated particle 200 (e.g., coating 230 of coated particle 200) includes a diagnostic agent (e.g., a radiopaque material, a material that is visible by magnetic resonance imaging (an MRI-visible material), an ultrasound contrast agent) and/or a ferromagnetic material. The diagnostic agent and/or the ferromagnetic material can, for example, be fed through the tube along with coating material 130 (e.g., as a mixture including coating material 130 and the diagnostic agent and/or the ferromagnetic material). Alternatively or additionally, one or more diagnostic agents and/or ferromagnetic materials can be included in particles 105. In some embodiments, the diagnostic agent and/or ferromagnetic material can be added to particle 105 by injection of the diagnostic agent and/or ferromagnetic material into particle 105 and/or by soaking particle 105 in the diagnostic agent and/or ferromagnetic material. Diagnostic agents and ferromagnetic materials are described in U.S. Patent Application Publication No. US 2004/0101564 A1, published on May 27, 2004, and entitled "Embolization", which is incorporated by reference herein.

As a further example, while the therapeutic agent was described above as being a component of coating material 130, the therapeutic agent can alternatively or additionally be added to particles 105. For example, the therapeutic agent can be added to particles 105 by injection of the therapeutic agent into particles 105 and/or by soaking particles 105 in the therapeutic agent before applying coating 230. The therapeutic agent, therefore, can be incorporated into gel coating 230 of coated particles 200, as described above, and/or the therapeutic agent can be loaded into the core region (e.g., into particle 105) of coated particles 200. In embodiments in which both coating 230 and particle 105 include the therapeutic agent, coating 230 can, during use, release an initial dosage of therapeutic agent after which particle 105 can provide a burst release of therapeutic agent. The therapeutic agent in coating 230 can be the same as or different from the therapeutic agent in particle 105.

While the therapeutic agent of many of the embodiments above is described as being TORADOL®, any of various other therapeutic agents can be used. Therapeutic agents include agents that are negatively charged, positively charged, amphoteric, or neutral. Therapeutic agents include genetic therapeutic agents, non-genetic therapeutic agents, and cells, and can be negatively charged, positively charged, amphoteric, or neutral. Therapeutic agents can be, for example, materials that are biologically active to treat physiological conditions; pharmaceutically active compounds; gene therapies; nucleic acids with and without carrier vectors; oligonucleotides; gene/vector systems; DNA chimeras; compacting agents (e.g., DNA compacting agents); viruses; polymers; hyaluronic acid; proteins (e.g., enzymes such as ribozymes); immunologic species; nonsteroidal anti-inflammatory medications; oral contraceptives; progestins; gonadotrophin-releasing hormone agonists; chemotherapeutic agents; and radioactive species (e.g., radioisotopes, radioactive molecules). Non-limiting examples of therapeutic agents include anti-thrombogenic agents; antioxidants; angiogenic and anti-angiogenic agents and factors; anti-proliferative agents (e.g., agents capable of blocking smooth muscle cell proliferation); calcium entry blockers; and survival genes which protect against cell death.

Exemplary non-genetic therapeutic agents include: anti-thrombotic agents such as heparin, heparin derivatives, urokinase, and PPack (dextrophenylalanine proline arginine chloromethylketone); anti-inflammatory agents such as dexamethasone, prednisolone, corticosterone, budesonide, estrogen, sulfasalazine and mesalamine; antineoplastic/antiproliferative/anti-mitotic agents such as paclitaxel, 5-fluorouracil, cisplatin, doxorubicin; vinblastine, vincristine, epothilones, endostatin, angiostatin, angiopeptin, monoclonal antibodies capable of blocking smooth muscle cell proliferation, and thymidine kinase inhibitors; anesthetic agents such as lidocaine, bupivacaine and ropivacaine; anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; vascular cell growth promoters such as growth factors, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; protein kinase and tyrosine kinase inhibitors (e.g., tyrphostins, genistein, quinoxalines); prostacyclin analogs; cholesterol-lowering agents; angiopoietins; antimicrobial agents such as triclosan, cephalosporins, aminoglycosides and nitrofurantoin; cytotoxic agents, cytostatic agents and cell proliferation affectors; vasodilating agents; and agents that interfere with endogenous vasoactive mechanisms.

Exemplary genetic therapeutic agents include: anti-sense DNA and RNA; DNA coding for: anti-sense RNA, tRNA or rRNA to replace defective or deficient endogenous molecules, angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor a, hepatocyte growth factor and insulin like growth factor, cell cycle inhibitors including CD inhibitors, thymidine kinase ("TK") and other agents useful for interfering with cell proliferation, and the family of bone morphogenic proteins ("BMP's"), including BMP2, BMP3, BMP4, BMP5, BMP6 (Vgr1), BMP7 (OP1), BMP8, BMP9, BMP10, BM11, BMP12, BMP13, BMP14, BMP15, and BMP16. Currently preferred BMP's are any of BMP2, BMP3, BMP4, BMP5, BMP6 and BMP7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

Vectors of interest for delivery of genetic therapeutic agents include: Plasmids, Viral vectors such as adenovirus (AV), adenoassociated virus (AAV) and lentivirus, Non-viral vectors such as lipids, liposomes and cationic lipids.

Cells include cells of human origin (autologous or allogeneic), including stem cells, or from an animal source (xenogeneic), which can be genetically engineered if desired to deliver proteins of interest.

Several of the above and numerous additional therapeutic agents appropriate for the practice of the present invention are disclosed in U.S. Pat. No. 5,733,925, which is incorporated herein by reference. Therapeutic agents disclosed in this patent include the following: "Cytostatic agents" (i.e., agents that prevent or delay cell division in proliferating cells, for example, by inhibiting replication of DNA or by inhibiting spindle fiber formation). Representative examples of cytostatic agents include modified toxins, methotrexate, adriamycin, radionuclides (e.g., such as disclosed in Fritzberg et al., U.S. Pat. No. 4,897,255), protein kinase inhibitors, including staurosporin, a protein kinase C inhibitor of the following formula:

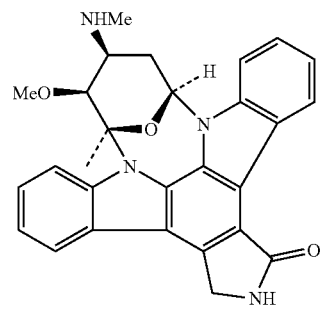 [SMILES: CN[C@H]1C[C@H]2O[C@@](C)([C@H]1OC)n1c3ccccc3c3c4c(c5c6ccccc6n2c5c31)C(=O)NC4]

as well as diindoloalkaloids having one of the following general structures:

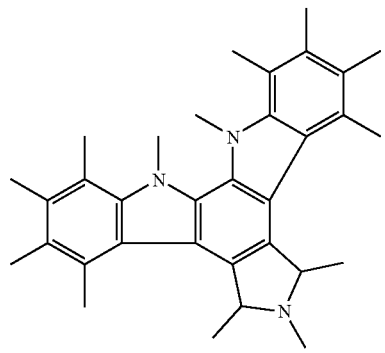

-continued

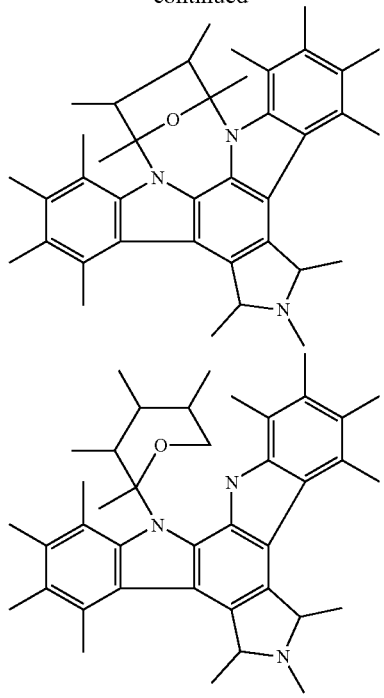

as well as stimulators of the production or activation of TGF-beta, including Tamoxifen and derivatives of functional equivalents (e.g., plasmin, heparin, compounds capable of reducing the level or inactivating the lipoprotein Lp(a) or the glycoprotein apolipoprotein(a)) thereof, TGF-beta or functional equivalents, derivatives or analogs thereof, suramin, nitric oxide releasing compounds (e.g., nitroglycerin) or analogs or functional equivalents thereof, paclitaxel or analogs thereof (e.g., taxotere), inhibitors of specific enzymes (such as the nuclear enzyme DNA topoisomerase II and DNA polymerase, RNA polymerase, adenyl guanyl cyclase), superoxide dismutase inhibitors, terminal deoxynucleotidyl-transferase, reverse transcriptase, antisense oligonucleotides that suppress smooth muscle cell proliferation and the like.

Other examples of "cytostatic agents" include peptidic or mimetic inhibitors (i.e., antagonists, agonists, or competitive or non-competitive inhibitors) of cellular factors that may (e.g., in the presence of extracellular matrix) trigger proliferation of smooth muscle cells or pericytes: e.g., cytokines (e.g., interleukins such as IL-1), growth factors (e.g., PDGF, TGF-alpha or -beta, tumor necrosis factor, smooth muscle- and endothelial-derived growth factors, i.e., endothelin, FGF), homing receptors (e.g., for platelets or leukocytes), and extracellular matrix receptors (e.g., integrins). Representative examples of useful therapeutic agents in this category of cytostatic agents addressing smooth muscle proliferation include: subfragments of heparin, triazolopyrimidine (trapidil; a PDGF antagonist), lovastatin, and prostaglandins E1 or I2.

Agents that inhibit the intracellular increase in cell volume (i.e., the tissue volume occupied by a cell) such as cytoskeletal inhibitors or metabolic inhibitors. Representative examples of cytoskeletal inhibitors include colchicine, vinblastin, cytochalasins, paclitaxel and the like, which act on microtubule and microfilament networks within a cell. Representative examples of metabolic inhibitors include staurosporin, trichothecenes, and modified diphtheria and ricin toxins, Pseudomonas exotoxin and the like. Trichothecenes include simple trichothecenes (i.e., those that have only a central sesquiterpenoid structure) and macrocyclic trichothecenes (i.e., those that have an additional macrocyclic ring), e.g., a verrucarins or roridins, including Verrucarin A, Verrucarin B, Verrucarin J (Satratoxin C), Roridin A, Roridin C, Roridin D, Roridin E (Satratoxin D), Roridin H.

Agents acting as an inhibitor that blocks cellular protein synthesis and/or secretion or organization of extracellular matrix (i.e., an "anti-matrix agent"). Representative examples of "anti-matrix agents" include inhibitors (i.e., agonists and antagonists and competitive and non-competitive inhibitors) of matrix synthesis, secretion and assembly, organizational cross-linking (e.g., transglutaminases cross-linking collagen), and matrix remodeling (e.g., following wound healing). A representative example of a useful therapeutic agent in this category of anti-matrix agents is colchicine, an inhibitor of secretion of extracellular matrix. Another example is tamoxifen for which evidence exists regarding its capability to organize and/or stabilize as well as diminish smooth muscle cell proliferation following angioplasty. The organization or stabilization may stem from the blockage of vascular smooth muscle cell maturation in to a pathologically proliferating form.

Agents that are cytotoxic to cells, particularly cancer cells. Examples of such agents are Roridin A, Pseudomonas exotoxin and the like or analogs or functional equivalents thereof. A plethora of such therapeutic agents, including radioisotopes and the like, have been identified and are known in the art. In addition, protocols for the identification of cytotoxic moieties are known and employed routinely in the art.

A number of the above therapeutic agents and several others have also been identified as candidates for vascular treatment regimens, for example, as agents targeting restenosis. Such agents are appropriate for the practice of the present invention and include one or more of the following:

Calcium-channel blockers including:
  Benzothiazapines such as diltiazem and clentiazem
  Dihydropyridines such as nifedipine, amlodipine and nicardapine
  Phenylalkylamines such as verapamil
Serotonin pathway modulators including:
  5-HT antagonists such as ketanserin and naftidrofuryl
  5-HT uptake inhibitors such as fluoxetine
Cyclic nucleotide pathway agents including:
  Phosphodiesterase inhibitors such as cilostazole and dipyridamole
  Adenylate/Guanylate cyclase stimulants such as forskolin
  Adenosine analogs
Catecholamine modulators including:
  α-antagonists such as prazosin and bunazosine
  β-antagonists such as propranolol
  α/β-antagonists such as labetalol and carvedilol
Endothelin receptor antagonists
Nitric oxide donors/releasing molecules including:
  Organic nitrates/nitrites such as nitroglycerin, isosorbide dinitrate and amyl nitrite
  Inorganic nitroso compounds such as sodium nitroprusside
  Sydnonimines such as molsidomine and linsidomine
  Nonoates such as diazenium diolates and NO adducts of alkanediamines
  S-nitroso compounds including low molecular weight compounds (e.g., S-nitroso derivatives of captopril, glutathione and N-acetyl penicillamine), high molecular weight compounds (e.g., S-nitroso derivatives of proteins, peptides, oligosaccharides, polysaccharides, synthetic polymers/oligomers and natural polymers/oligomers)

C-nitroso-, O-nitroso- and N-nitroso-compounds

L-arginine

ACE inhibitors such as cilazapril, fosinopril and enalapril

ATII-receptor antagonists such as saralasin and losartin

Platelet adhesion inhibitors such as albumin and polyethylene oxide

Platelet aggregation inhibitors including:
Aspirin and thienopyridine (ticlopidine, clopidogrel)
GP IIb/IIIa inhibitors such as abciximab, epitifibatide and tirofiban
Coagulation pathway modulators including:
Heparinoids such as heparin, low molecular weight heparin, dextran sulfate and β-cyclodextrin tetradecasulfate
Thrombin inhibitors such as hirudin, hirulog, PPACK (D-phe-L-propyl-L-arg-chloromethylketone) and argatroban
FXa inhibitors such as antistatin and TAP (tick anticoagulant peptide)
Vitamin K inhibitors such as warfarin
Activated protein C
Cyclooxygenase pathway inhibitors such as aspirin, ibuprofen, flurbiprofen, indomethacin and sulfinpyrazone
Natural and synthetic corticosteroids such as dexamethasone, prednisolone, methprednisolone and hydrocortisone
Lipoxygenase pathway inhibitors such as nordihydroguairetic acid and caffeic acid
Leukotriene receptor antagonists
Antagonists of E- and P-selectins
Inhibitors of VCAM-1 and ICAM-1 interactions
Prostaglandins and analogs thereof including:
Prostaglandins such as PGE1 and PGI2
Prostacyclin analogs such as ciprostene, epoprostenol, carbacyclin, iloprost and beraprost
Macrophage activation preventers including bisphosphonates
HMG-CoA reductase inhibitors such as lovastatin, pravastatin, fluvastatin, simvastatin and cerivastatin
Fish oils and omega-3-fatty acids
Free-radical scavengers/antioxidants such as probucol, vitamins C and E, ebselen, trans-retinoic acid and SOD mimics
Agents affecting various growth factors including:
FGF pathway agents such as bFGF antibodies and chimeric fusion proteins

PDGF receptor antagonists such as trapidil
IGF pathway agents including somatostatin analogs such as angiopeptin and ocreotide
TGF-β pathway agents such as polyanionic agents (heparin, fucoidin), decorin, and TGF-β antibodies
EGF pathway agents such as EGF antibodies, receptor antagonists and chimeric fusion proteins
TNF-α pathway agents such as thalidomide and analogs thereof.
Thromboxane A2 (TXA2) pathway modulators such as sulotroban, vapiprost, dazoxiben and ridogrel
Protein tyrosine kinase inhibitors such as tyrphostin, genistein and quinoxaline derivatives
MMP pathway inhibitors such as marimastat, ilomastat and metastat
Cell motility inhibitors such as cytochalasin B
Antiproliferative/antineoplastic agents including:
Antimetabolites such as purine analogs(6-mercaptopurine), pyrimidine analogs (e.g., cytarabine and 5-fluorouracil) and methotrexate
Nitrogen mustards, alkyl sulfonates, ethylenimines, antibiotics (e.g., daunorubicin, doxorubicin), nitrosoureas and cisplatin
Agents affecting microtubule dynamics (e.g., vinblastine, vincristine, colchicine, paclitaxel and epothilone)
Caspase activators
Proteasome inhibitors
Angiogenesis inhibitors (e.g., endostatin, angiostatin and squalamine)
Rapamycin, cerivastatin, flavopiridol and suramin
Matrix deposition/organization pathway inhibitors such as halofuginone or other quinazolinone derivatives and tranilast
Endothelialization facilitators such as VEGF and RGD peptide
Blood rheology modulators such as pentoxifylline.

Therapeutic agents are described, for example, in co-pending Published Patent Application No. US 2004/0076582 A1, published on Apr. 22, 2004, and entitled "Agent Delivery Particle", which is incorporated herein by reference, and in Pinchuk et al., U.S. Pat. No. 6,545,097, which is incorporated herein by reference.

Other embodiments are in the claims.

What is claimed is:

1. A method, comprising:
injecting pulses of gas into a container, wherein the container contains a continuous stream of a coating material, thereby forming a discontinuous stream of the coating material within a container, the discontinuous stream comprising multiple discrete portions of the coating material;
introducing a particle having a diameter of 3,000 microns or less into the container after the coating material has been introduced into the container; and
disposing the particle in one of the discrete portions of the coating material within the container.

2. The method of claim 1, further comprising disposing one particle in each of the multiple discrete portions of the coating material.

3. The method of claim 1, further comprising the step of cross-linking a polymer within the particle; and then introducing the particle into the container.

* * * * *